(12) United States Patent
Kwon et al.

(10) Patent No.: US 8,450,274 B2
(45) Date of Patent: May 28, 2013

(54) DKK2 PROTEIN AND USE THEREOF

(75) Inventors: Young-Guen Kwon, Seoul (KR); Jeong-Ki Min, Gangwon-do (KR)

(73) Assignee: Theragenetex Co., Ltd., Siheung-si (JP)

( * ) Notice: Subject to any disclaimer, the term of this patent is extended or adjusted under 35 U.S.C. 154(b) by 95 days.

(21) Appl. No.: 13/091,007

(22) Filed: Apr. 20, 2011

(65) Prior Publication Data

US 2011/0223184 A1     Sep. 15, 2011

Related U.S. Application Data

(63) Continuation-in-part of application No. 12/302,277, filed as application No. PCT/KR2007/002493 on May 23, 2007, now Pat. No. 8,067,387.

(60) Provisional application No. 61/326,509, filed on Apr. 21, 2010.

(30) Foreign Application Priority Data

Mar. 14, 2011 (KR) .................. 10-2011-0022442
Mar. 14, 2011 (KR) .................. 10-2011-0022443

(51) Int. Cl.
*A61K 38/00* (2006.01)
*A61K 39/00* (2006.01)
*A61P 17/02* (2006.01)
*C07K 17/02* (2006.01)

(52) U.S. Cl.
USPC .......... 514/13.3; 514/7.6; 514/9.4; 424/198.1

(58) Field of Classification Search
None
See application file for complete search history.

(56) References Cited

U.S. PATENT DOCUMENTS

| | | | | |
|---|---|---|---|---|
| 6,344,541 | B1 * | 2/2002 | Bass et al. ........... | 530/324 |
| 2004/0014209 | A1 * | 1/2004 | Lassar et al. ........ | 435/366 |
| 2005/0261181 | A1 * | 11/2005 | Wu et al. ............. | 514/12 |

FOREIGN PATENT DOCUMENTS

| | | |
|---|---|---|
| EP | 2 098 244 A1 | 9/2009 |
| KR | 10-2007-0113500 | 11/2007 |
| KR | 10-2008-0085908 | 9/2008 |

OTHER PUBLICATIONS

Niehrs, C., Oncogene, 25(57): 7469-7481, Dec. 4, 2006.

\* cited by examiner

*Primary Examiner* — Daniel C Gamett
(74) *Attorney, Agent, or Firm* — Joseph Hyosuk Kim; JHK Law

(57) ABSTRACT

The present invention provides DKK2 and DKK-Fc fusion protein with angiogesis promoting activity and methods of using the same.

7 Claims, 43 Drawing Sheets

DKK2-transgenic mouse

SEQUENCE LISTING

```
<160> NUMBER OF SEQ ID NOS: 32

<210> SEQ ID NO 1
<211> LENGTH: 259
<212> TYPE: PRT
<213> ORGANISM: Homo sapiens

<400> SEQUENCE: 1

Met Ala Ala Leu Met Arg Ser Lys Asp Ser Ser Cys Cys Leu Leu Leu
1               5                   10                  15

Leu Ala Ala Val Leu Met Val Glu Ser Ser Gln Ile Gly Ser Ser Arg
            20                  25                  30

Ala Lys Leu Asn Ser Ile Lys Ser Ser Leu Gly Gly Glu Thr Pro Gly
        35                  40                  45

Gln Ala Ala Asn Arg Ser Ala Gly Met Tyr Gln Gly Leu Ala Phe Gly
    50                  55                  60

Gly Ser Lys Lys Gly Lys Asn Leu Gly Gln Ala Tyr Pro Cys Ser Ser
65                  70                  75                  80

Asp Lys Glu Cys Glu Val Gly Arg Tyr Cys His Ser Pro His Gln Gly
                85                  90                  95

Ser Ser Ala Cys Met Val Cys Arg Arg Lys Lys Lys Arg Cys His Arg
            100                 105                 110

Asp Gly Met Cys Cys Pro Ser Thr Arg Cys Asn Asn Gly Ile Cys Ile
        115                 120                 125

Pro Val Thr Glu Ser Ile Leu Thr Pro His Ile Pro Ala Leu Asp Gly
    130                 135                 140

Thr Arg His Arg Asp Arg Asn His Gly His Tyr Ser Asn His Asp Leu
145                 150                 155                 160

Gly Trp Gln Asn Leu Gly Arg Pro His Thr Lys Met Ser His Ile Lys
                165                 170                 175

Gly His Glu Gly Asp Pro Cys Leu Arg Ser Ser Asp Cys Ile Glu Gly
            180                 185                 190

Phe Cys Cys Ala Arg His Phe Trp Thr Lys Ile Cys Lys Pro Val Leu
        195                 200                 205

His Gln Gly Glu Val Cys Thr Lys Gln Arg Lys Lys Gly Ser His Gly
    210                 215                 220

Leu Glu Ile Phe Gln Arg Cys Asp Cys Ala Lys Gly Leu Ser Cys Lys
225                 230                 235                 240

Val Trp Lys Asp Ala Thr Tyr Ser Ser Lys Ala Arg Leu His Val Cys
                245                 250                 255

Gln Lys Ile

<210> SEQ ID NO 2
<211> LENGTH: 3659
<212> TYPE: DNA
<213> ORGANISM: Homo sapiens
```

<400> SEQUENCE: 2

```
cgggagcccg cggcgagcgt agcgcaagtc cgctccctag gcatcgctgc gctggcagcg      60
attcgctgtc tcttgtgagt caggggacaa cgcttcgggg caactgtgag tgcgcgtgtg     120
ggggacctcg attctcttca gatctcgagg attcggtccg gggacgtctc ctgatcccct     180
actaaagcgc ctgctaactt tgaaaaggag cactgtgtcc tgcaaagttt gacacataaa     240
ggataggaaa agagaggaga gaaaagcaac tgagttgaag gagaaggagc tgatgcgggc     300
ctcctgatca attaagagga gagttaaacc gccgagatcc cggcgggacc aaggaggtgc     360
ggggcaagaa ggaacggaag cggtgcgatc cacagggctg ggttttcttg cacctgggt      420
cacgcctcct tggcgagaaa cgcctcgca tttgattgct tccagttatt gcagaacttc      480
ctgtcctggt ggagaagcgg gtctcgcttg ggttccgcta atttctgtcc tgaggcgtga     540
gactgagttc atagggtcct gggtccccga accaggaagg gttgagggaa cacaatctgc     600
aagcccccgc gacccaagtg aggggccccg tgttgggggtc ctccctccct ttgcattccc    660
accctccgg gctttgcgtc ttcctgggga cccctcgcc gggagatggc cgcgttgatg       720
cggagcaagg attcgtcctg ctgcctgctc ctactggccg cggtgctgat ggtggagagc     780
tcacagatcg gcagttcgcg ggccaaactc aactccatca agtcctctct gggcggggag     840
acgcctggtc aggccgccaa tcgatctgcg ggcatgtacc aaggactggc attcggcggc     900
agtaagaagg gcaaaaacct ggggcaggcc taccttgta gcagtgataa ggagtgtgaa       960
gttgggaggt attgccacag tccccaccaa ggatcatcgg cctgcatggt gtgtcggaga    1020
aaaagaagc gctgccaccg agatggcatg tgctgcccca gtaccgctg caataatggc      1080
atctgtatcc cagttactga aagcatctta accctcaca tcccggctct ggatggtact     1140
cggcacagag atcgaaacca cggtcattac tcaaaccatg acttgggatg cagaatcta     1200
ggaagaccac acactaagat gtcacatata aagggcatg aaggagaccc ctgcctacga    1260
tcatcagact gcattgaagg ttttgctgt gctcgtcatt tctggaccaa aatctgcaaa    1320
ccagtgctcc atcagggga agtctgtacc aaacaacgca agaagggttc tcatgggctg    1380
gaaattttcc agcgttgcga ctgtgcgaag ggcctgtctt gcaaagtatg gaaagatgcc    1440
acctactcct ccaaagccag actccatgtg tgtcagaaaa tttgatcacc attgaggaac    1500
atcatcaatt gcagactgtg aagttgtgta tttaatgcat tatagcatgg tggaaaataa    1560
ggttcagatg cagaagaatg gctaaaataa gaaacgtgat aagaatatag atgatcacaa    1620
aaagggagaa agaaaacatg aactgaatag attagaatgg gtgacaaatg cagtgcagcc    1680
agtgttttcca ttatgcaact tgtctatgta aataatgtac acatttgtgg aaaatgctat   1740
tattaagaga acaagcacac agtggaaatt actgatgagt agcatgtgac tttccaagag    1800
tttaggttgt gctggaggag aggtttcctt cagattgctg attgcttata caataaccct    1860
acatgccaga tttctattca acgttagagt ttaacaaaat actcctagaa taacttgtta    1920
tacaataggt tctaaaaata aaattgctaa acaagaaatg aaaacatgga gcattgttaa    1980
tttacaacag aaaattacct tttgatttgt aacactactt ctgctgttca atcaagagtc    2040
ttggtagata agaaaaaaat cagtcaatat ttccaaataa ttgcaaaata atggccagtt    2100
gtttaggaag gcctttagga agacaaataa ataacaaaca aacagccaca aatacttttt    2160
tttcaaaatt ttagttttac ctgtaattaa taagaactga tacaagacaa aaacagttcc    2220
ttcagattct acggaatgac agtatatctc tctttatcct atgtgattcc tgctctgaat    2280
gcattatatt ttccaaacta tacccataaa ttgtgactag taaaatactt acacagagca    2340
```

-continued

```
gaattttcac agatggcaaa aaaatttaaa gatgtccaat atatgtggga aagagctaa      2400 cagagagatc attatttctt aaagattggc cataacctgt attttgatag aattagattg     2460
gtaaatacat gtattcatac atactctgtg gtaatagaga cttgagctgg atctgtactg     2520
cactggagta agcaagaaaa ttgggaaaac ttttcgttt gttcaggttt tggcaacaca      2580
tagatcatat gtctgaggca caagttggct gttcatcttt gaaaccaggg gatgcacagt    2640
ctaaatgaat atctgcatgg gatttgctat cataatattt actatgcaga tgaattcagt   2700
gtgaggtcct gtgtccgtac tatcctcaaa ttatttattt tatagtgctg agatcctcaa    2760
ataatctcaa tttcaggagg tttcacaaaa tggactcctg aagtagacag agtagtgagg   2820
tttcattgcc ctctataagc ttctgactag ccaatggcat catccaattt tcttcccaaa   2880
cctctgcagc atctgcttta ttgccaaagg gctagtttcg gttttctgca gccattgcgg   2940
ttaaaaaata taagtaggat aacttgtaaa acctgcatat tgctaatcta tagacaccac    3000
agtttctaaa ttctttgaaa ccactttact acttttttta aacttaactc agttctaaat    3060
actttgtctg gagcacaaaa caataaaagg ttatcttata gtcgtgactt taaacttttg    3120
tagaccacaa ttcactttt agttttcttt tacttaaatc ccatctgcag tctcaaattt   3180
aagttctccc agtagagatt gagtttgagc ctgtatatct attaaaaatt tcaacttccc    3240
acatatattt actaagatga ttaagactta cattttctgc acaggtctgc aaaaacaaaa    3300
attataaact agtccatcca agaaccaaag tttgtataaa caggttgcta taagcttggt    3360
gaaatgaaaa tggaacattt caatcaaaca tttcctatat aacaattatt atatttacaa   3420
tttggtttct gcaatatttt tcttatgtcc acccttttaa aaattattat ttgaagtaat    3480
ttatttacag gaaatgttaa tgagatgtat tttcttatag agatatttct tacagaaagc    3540
tttgtagcag aatatatttg cagctattga ctttgtaatt taggaaaaat gtataataag    3600
ataaaatcta ttaaatttt ctcctctaaa aactgaaaaa aaaaaaaaaa aaaaaaaa       3659
```

```
<210> SEQ ID NO 3
<211> LENGTH: 474
<212> TYPE: PRT
<213> ORGANISM: Artificial Sequence
<220> FEATURE:
<223> OTHER INFORMATION: DKK2-Fc fusion protein

<400> SEQUENCE: 3

Ser Phe Phe Phe Leu Phe Glu Lys Arg Lys Leu Asn Ser Ile Lys Ser
1               5                   10                  15

Ser Leu Gly Gly Glu Thr Pro Gly Gln Ala Ala Asn Arg Ser Ala Gly
                20                  25                  30

Met Tyr Gln Gly Leu Ala Phe Gly Gly Ser Lys Lys Gly Lys Asn Leu
            35                  40                  45

Gly Gln Ala Tyr Pro Cys Ser Ser Asp Lys Glu Cys Glu Val Gly Arg
        50                  55                  60

Tyr Cys His Ser Pro His Gln Gly Ser Ser Ala Cys Met Val Cys Arg
65                  70                  75                  80

Arg Lys Lys Lys Arg Cys His Arg Asp Gly Met Cys Cys Pro Ser Thr
                85                  90                  95

Arg Cys Asn Asn Gly Ile Cys Ile Pro Val Thr Glu Ser Ile Leu Thr
            100                 105                 110

Pro His Ile Pro Ala Leu Asp Gly Thr Arg His Arg Asp Arg Asn His
        115                 120                 125

Gly His Tyr Ser Asn His Asp Leu Gly Trp Gln Asn Leu Gly Arg Pro
```

130              135              140
His Thr Lys Met Ser His Ile Lys Gly His Glu Gly Asp Pro Cys Leu
145                  150                  155                  160

Arg Ser Ser Asp Cys Ile Glu Gly Phe Cys Cys Ala Arg His Phe Trp
                165                  170                  175

Thr Lys Ile Cys Lys Pro Val Leu His Gln Gly Glu Val Cys Thr Lys
                180                  185                  190

Gln Arg Lys Lys Gly Ser His Gly Leu Glu Ile Phe Gln Arg Cys Asp
                195                  200                  205

Cys Ala Lys Gly Leu Ser Cys Lys Val Trp Lys Asp Ala Thr Tyr Ser
210                  215                  220

Ser Lys Ala Arg Leu His Val Cys Gln Lys Ile Leu Glu Ser Arg Leu
225                  230                  235                  240

Val Pro Arg Gly Ser Ala Ser Asp Lys Thr His Thr Cys Pro Pro Cys
                245                  250                  255

Pro Ala Pro Glu Leu Leu Gly Gly Pro Ser Val Phe Leu Phe Pro Pro
                260                  265                  270

Lys Pro Lys Asp Thr Leu Met Ile Ser Arg Thr Pro Glu Val Thr Cys
                275                  280                  285

Val Val Val Asp Val Ser His Glu Asp Pro Glu Val Lys Phe Asn Trp
                290                  295                  300

Tyr Val Asp Gly Val Glu Val His Asn Ala Lys Thr Lys Pro Arg Glu
305                  310                  315                  320

Glu Gln Tyr Asn Ser Thr Tyr Arg Val Val Ser Val Leu Thr Val Leu
                325                  330                  335

His Gln Asp Trp Leu Asn Gly Lys Glu Tyr Lys Cys Lys Val Ser Asn
                340                  345                  350

Lys Ala Leu Pro Ala Pro Ile Glu Lys Thr Ile Ser Lys Ala Lys Gly
                355                  360                  365

Gln Pro Arg Glu Pro Gln Val Tyr Thr Leu Pro Pro Ser Arg Asp Glu
                370                  375                  380

Leu Thr Lys Asn Gln Val Ser Leu Thr Cys Leu Val Lys Gly Phe Tyr
385                  390                  395                  400

Pro Ser Asp Ile Ala Val Glu Trp Glu Ser Asn Gly Gln Pro Glu Asn
                405                  410                  415

Asn Tyr Lys Thr Thr Pro Pro Val Leu Asp Ser Asp Gly Ser Phe Phe
                420                  425                  430

Leu Tyr Ser Lys Leu Thr Val Asp Lys Ser Arg Trp Gln Gln Gly Asn
                435                  440                  445

Val Phe Ser Cys Ser Val Met His Glu Ala Leu His Asn His Tyr Thr
450                  455                  460

Gln Lys Ser Leu Ser Leu Ser Pro Gly Lys
465                  470

<210> SEQ ID NO 4
<211> LENGTH: 1638
<212> TYPE: DNA
<213> ORGANISM: Artificial Sequence
<220> FEATURE:
<223> OTHER INFORMATION: DKK2-Fc fusion gene

<400> SEQUENCE: 4
agtctttttt ttttcttttc gagaaaagga aactcaactc catcaagtcc tctctgggcg    60
gggagacgcc tggtcaggcc gccaatcgat ctgcgggcat gtaccaagga ctggcattcg   120
gcggcagtaa gaagggcaaa aacctggggc aggcctaccc ttgtagcagt gataaggagt   180

```
gtgaagttgg gaggtattgc cacagtcccc accaaggatc atcggcctgc atggtgtgtc    240
ggagaaaaaa gaagcgctgc caccgagatg gcatgtgctg ccccagtacc cgctgcaata    300
atggcatctg tatcccagtt actgaaagca tcttaacccc tcacatcccg gctctggatg    360
gtactcggca cagagatcga aaccacggtc attactcaaa ccatgacttg ggatggcaga    420
atctaggaag accacacact aagatgtcac atataaaagg gcatgaagga daccctgcc    480 tacgatcatc agactgcatt gaagggtttt gctgtgctcg tcatttctgg accaaaatct    540
gcaaaccagt gctccatcag ggggaagtct gtaccaaaca acgcaagaag ggttctcatg    600
ggctggaaat tttccagcgt tgcgactgtg cgaagggcct gtcttgcaaa gtatggaaag    660
atgccaccta ctcctccaaa gccagactcc atgtgtgtca gaaaattctc gagtctagac    720
tggtgccgcg cggcagcgct agcgacaaaa ctcacacatg cccaccgtgc ccagcacctg    780
aactcctggg gggaccgtca gtcttcctct tccccccaaa acccaaggac accctcatga    840
tctcccggac ccctgaggtc acatgcgtgg tggtggacgt gagccacgaa gaccctgagg    900
tcaagttcaa ctggtacgtg gacggcgtgg aggtgcataa tgccaagaca aagccgcggg    960
aggagcagta caacagcacg taccgtgtgg tcagcgtcct caccgtcctg caccaggact   1020
ggctgaatgg caaggagtac aagtgcaagg tctccaacaa agccctccca gcccccatcg   1080
agaaaaccat ctccaaagcc aaagggcagc cccgagaacc acaggtgtac accctgcccc   1140
catcccggga tgagctgacc aagaaccagg tcagcctgac ctgcctggtc aaaggcttct   1200
atcccagcga catcgccgtg gagtgggaga gcaatgggca gccggagaac aactacaaga   1260
ccacgcctcc cgtgctggac tccgacggct ccttcttcct ctacagcaag ctcaccgtgg   1320
acaagagcag gtggcagcag gggaacgtct tctcatgctc cgtgatgcat gaggctctgc   1380
acaaccacta cacgcagaag agcctctccc tgtccccggg taaatgaggt accggccggc   1440
catttaaata caggccccctt ttcctttgtc gatatcatgt aattagttat gtcacgctta   1500
cattcacgcc ctcctcccac atccgctcta accgaaaagg aaggagttag acaacctgaa   1560
gtctaggtcc ctatttattt tttttaatag ttatgttagt attaagaacg ttatttatat   1620
ttcaaatttt cagggtgg                                                 1638
```

<210> SEQ ID NO 5
<211> LENGTH: 20
<212> TYPE: DNA
<213> ORGANISM: Artificial Sequence
<220> FEATURE:
<223> OTHER INFORMATION: mDKK2_A primer

<400> SEQUENCE: 5

```
cagagatggg atgtgttgcc                                                 20
```

<210> SEQ ID NO 6
<211> LENGTH: 20
<212> TYPE: DNA
<213> ORGANISM: Artificial Sequence
<220> FEATURE:
<223> OTHER INFORMATION: mDKK2_A primer

<400> SEQUENCE: 6

```
cctgatggag cactggtttg                                                 20
```

<210> SEQ ID NO 7
<211> LENGTH: 20
<212> TYPE: DNA
<213> ORGANISM: Artificial Sequence

```
<220> FEATURE:
<223> OTHER INFORMATION: mDKK2_B primer

<400> SEQUENCE: 7
gatgggtttt gttgtgctcg                                          20

<210> SEQ ID NO 8
<211> LENGTH: 20
<212> TYPE: DNA
<213> ORGANISM: Artificial Sequence
<220> FEATURE:
<223> OTHER INFORMATION: mDKK2_B primer

<400> SEQUENCE: 8
atgtttcagg ttcaggggga                                          20

<210> SEQ ID NO 9
<211> LENGTH: 20
<212> TYPE: DNA
<213> ORGANISM: Artificial Sequence
<220> FEATURE:
<223> OTHER INFORMATION: mGAPDH primer

<400> SEQUENCE: 9
cgccacagtt tcccggaggg                                          20

<210> SEQ ID NO 10
<211> LENGTH: 20
<212> TYPE: DNA
<213> ORGANISM: Artificial Sequence
<220> FEATURE:
<223> OTHER INFORMATION: mGAPDH primer

<400> SEQUENCE: 10
ccctccaaaa tcaagtgggg                                          20

<210> SEQ ID NO 11
<211> LENGTH: 20
<212> TYPE: DNA
<213> ORGANISM: Artificial Sequence
<220> FEATURE:
<223> OTHER INFORMATION: DKK1 primer

<400> SEQUENCE: 11
cctggagtgt aagagctttg                                          20

<210> SEQ ID NO 12
<211> LENGTH: 18
<212> TYPE: DNA
<213> ORGANISM: Artificial Sequence
<220> FEATURE:
<223> OTHER INFORMATION: DKK1 primer

<400> SEQUENCE: 12
ccaagagatc cttgcgtt                                            18

<210> SEQ ID NO 13
<211> LENGTH: 20
<212> TYPE: DNA
<213> ORGANISM: Artificial Sequence
<220> FEATURE:
<223> OTHER INFORMATION: DKK2 primer

<400> SEQUENCE: 13
tagagattga gtttgagcct                                          20
```

```
<210> SEQ ID NO 14
<211> LENGTH: 19
<212> TYPE: DNA
<213> ORGANISM: Artificial Sequence
<220> FEATURE:
<223> OTHER INFORMATION: DKK2 primer

<400> SEQUENCE: 14
aaagggtgga cataagaaa                                                  19

<210> SEQ ID NO 15
<211> LENGTH: 18
<212> TYPE: DNA
<213> ORGANISM: Artificial Sequence
<220> FEATURE:
<223> OTHER INFORMATION: KREMEN 2 primer

<400> SEQUENCE: 15
caccgactgt gaccagat                                                   18

<210> SEQ ID NO 16
<211> LENGTH: 19
<212> TYPE: DNA
<213> ORGANISM: Artificial Sequence
<220> FEATURE:
<223> OTHER INFORMATION: KREMEN2 primer

<400> SEQUENCE: 16
gagtagatga cgccctgag                                                  19

<210> SEQ ID NO 17
<211> LENGTH: 20
<212> TYPE: DNA
<213> ORGANISM: Artificial Sequence
<220> FEATURE:
<223> OTHER INFORMATION: LRP6 primer

<400> SEQUENCE: 17
gtccttccac tcataggtca                                                 20

<210> SEQ ID NO 18
<211> LENGTH: 20
<212> TYPE: DNA
<213> ORGANISM: Artificial Sequence
<220> FEATURE:
<223> OTHER INFORMATION: LRP6 primer

<400> SEQUENCE: 18
gtgggtagag gtgatgagaa                                                 20

<210> SEQ ID NO 19
<211> LENGTH: 20
<212> TYPE: DNA
<213> ORGANISM: Artificial Sequence
<220> FEATURE:
<223> OTHER INFORMATION: LRP5 primer

<400> SEQUENCE: 19
gggtggtgtc tattttgtgt                                                 20

<210> SEQ ID NO 20
<211> LENGTH: 20
<212> TYPE: DNA
<213> ORGANISM: Artificial Sequence
<220> FEATURE:
<223> OTHER INFORMATION: LRP5 primer

<400> SEQUENCE: 20
```

```
ccggaatgtt tgaagagtag                                              20

<210> SEQ ID NO 21
<211> LENGTH: 20
<212> TYPE: DNA
<213> ORGANISM: Artificial Sequence
<220> FEATURE:
<223> OTHER INFORMATION: APC primer

<400> SEQUENCE: 21
caggcaaaac aaaatgtggg                                              20

<210> SEQ ID NO 22
<211> LENGTH: 20
<212> TYPE: DNA
<213> ORGANISM: Artificial Sequence
<220> FEATURE:
<223> OTHER INFORMATION: APC primer

<400> SEQUENCE: 22
cgcttaggac tttgggttcc                                              20

<210> SEQ ID NO 23
<211> LENGTH: 20
<212> TYPE: DNA
<213> ORGANISM: Artificial Sequence
<220> FEATURE:
<223> OTHER INFORMATION: Asef2 primer

<400> SEQUENCE: 23
tctactcggg ggagctgact                                              20

<210> SEQ ID NO 24
<211> LENGTH: 20
<212> TYPE: DNA
<213> ORGANISM: Artificial Sequence
<220> FEATURE:
<223> OTHER INFORMATION: Asef2 primer

<400> SEQUENCE: 24
cctgcttcct ctgcagttca                                              20

<210> SEQ ID NO 25
<211> LENGTH: 20
<212> TYPE: DNA
<213> ORGANISM: Artificial Sequence
<220> FEATURE:
<223> OTHER INFORMATION: GAPDH primer

<400> SEQUENCE: 25
cgccacagtt tcccggaggg                                              20

<210> SEQ ID NO 26
<211> LENGTH: 20
<212> TYPE: DNA
<213> ORGANISM: Artificial Sequence
<220> FEATURE:
<223> OTHER INFORMATION: GAPDH primer

<400> SEQUENCE: 26
ccctccaaaa tcaagtgggg                                              20

<210> SEQ ID NO 27
<211> LENGTH: 4818
<212> TYPE: DNA
<213> ORGANISM: Artificial Sequence
```

<220> FEATURE:
<223> OTHER INFORMATION: pGL3 basic vector

<400> SEQUENCE: 27

```
ggtaccgagc tcttacgcgt gctagcccgg gctcgagatc tgcgatctaa gtaagcttgg     60
cattccggta ctgttggtaa agccaccatg gaagacgcca aaaacataaa gaaaggcccg    120
gcgccattct atccgctgga agatggaacc gctggagagc aactgcataa ggctatgaag    180
agatacgccc tggttcctgg aacaattgct tttacagatg cacatatcga ggtggacatc    240
acttacgctg agtacttcga aatgtccgtt cggttggcag aagctatgaa acgatatggg    300
ctgaatacaa atcacagaat cgtcgtatgc agtgaaaact ctcttcaatt ctttatgccg    360
gtgttgggcg cgttatttat cggagttgca gttgcgcccg cgaacgacat ttataatgaa    420
cgtgaattgc tcaacagtat gggcatttcg cagcctaccg tggtgttcgt ttccaaaaag    480
gggttgcaaa aatttttgaa cgtgcaaaaa aagctcccaa tcatccaaaa aattattatc    540
atggattcta aaacggatta ccagggattt cagtcgatgt acacgttcgt cacatctcat    600
ctacctcccg gttttaatga atacgatttt gtgccagagt ccttcgatag ggacaagaca    660
attgcactga tcatgaactc ctctggatct actggtctgc ctaaaggtgt cgctctgcct    720
catagaactg cctgcgtgag attctcgcat gccagagatc ctattttggg caatcaaatc    780
attccggata ctgcgatttt aagtgttgtt ccattccatc acggttttgg aatgtttact    840
acactcggat atttgatatg tggatttcga gtcgtcttaa tgtatagatt tgaagaagag    900
ctgtttctga ggagccttca ggattacaag attcaaagtg cgctgctggt gccaacccta    960
ttctccttct tcgccaaaag cactctgatt gacaaatacg atttatctaa tttacacgaa   1020
attgcttctg gtggcgctcc cctctctaag gaagtcgggg aagcggttgc caagaggttc   1080
catctgccag gtatcaggca aggatatggg ctcactgaga ctacatcagc tattctgatt   1140
acacccgagg gggatgataa accgggcgcg gtcggtaaag ttgttccatt ttttgaagcg   1200
aaggttgtgg atctggatac cgggaaaacg ctgggcgtta atcaaagagg cgaactgtgt   1260
gtgagaggtc ctatgattat gtccggttat gtaaacaatc cggaagcgac caacgccttg   1320
attgacaagg atggatggct acattctgga gacatagctt actgggacga agacgaacac   1380
ttcttcatcg ttgaccgcct gaagtctctg attaagtaca aaggctatca ggtggctccc   1440
gctgaattgg aatccatctt gctccaacac cccaacatct tcgacgcagg tgtcgcaggt   1500
cttcccgacg atgacgccgg tgaacttccc gccgccgttg ttgttttgga gcacggaaag   1560
acgatgacgg aaaaagagat cgtggattac gtcgccagtc aagtaacaac cgcgaaaaag   1620
ttgcgcggag gagttgtgtt tgtggacgaa gtaccgaaag gtcttaccgg aaaactcgac   1680
gcaagaaaaa tcagagagat cctcataaag gccaagaagg gcggaaagat cgccgtgtaa   1740
ttctagagtc ggggcggccg ccgcttcga gcagacatga taagatacat tgatgagttt   1800
ggacaaacca caactagaat gcagtgaaaa aaatgcttta tttgtgaaat ttgtgatgct   1860
attgctttat ttgtaaccat tataagctgc aataaacaag ttaacaacaa caattgcatt   1920
cattttatgt ttcaggttca gggggaggtg tgggaggttt tttaaagcaa gtaaaacctc   1980
tacaaatgtg gtaaaatcga taaggatccg tcgaccgatg cccttgagag ccttcaaccc   2040
agtcagctcc ttccggtggg cgcggggcat gactatcgtc gccgcactta tgactgtctt   2100
ctttatcatg caactcgtag gacaggtgcc ggcagcgctc ttccgcttcc tcgctcactg   2160
actcgctgcg ctcggtcgtt cggctgcggc gagcggtatc agctcactca aaggcggtaa   2220
tacggttatc cacagaatca ggggataacg caggaaagaa catgtgagca aaaggccagc   2280
```

```
aaaaggccag gaaccgtaaa aaggccgcgt tgctggcgtt tttccatagg ctccgccccc    2340
ctgacgagca tcacaaaaat cgacgctcaa gtcagaggtg gcgaaacccg acaggactat    2400
aaagatacca ggcgtttccc cctggaagct ccctcgtgcg ctctcctgtt ccgaccctgc    2460
cgcttaccgg atacctgtcc gcctttctcc cttcgggaag cgtggcgctt tctcatagct    2520
cacgctgtag gtatctcagt tcggtgtagg tcgttcgctc caagctgggc tgtgtgcacg    2580
aaccccccgt tcagcccgac cgctgcgcct tatccggtaa ctatcgtctt gagtccaacc    2640
cggtaagaca cgacttatcg ccactggcag cagccactgg taacaggatt agcagagcga    2700
ggtatgtagg cggtgctaca gagttcttga agtggtggcc taactacggc tacactagaa    2760
gaacagtatt tggtatctgc gctctgctga agccagttac cttcggaaaa agagttggta    2820
gctcttgatc cggcaaacaa accaccgctg gtagcggtgg ttttttgtt tgcaagcagc    2880 agattacgcg cagaaaaaaa ggatctcaag aagatccttt gatcttttct acggggtctg    2940
acgctcagtg aacgaaaac tcacgttaag ggattttggt catgagatta tcaaaaagga    3000
tcttcaccta gatccttta aattaaaaat gaagttttaa atcaatctaa agtatatatg    3060
agtaaacttg gtctgacagt taccaatgct taatcagtga ggcacctatc tcagcgatct    3120
gtctatttcg ttcatccata gttgcctgac tccccgtcgt gtagataact acgatacggg    3180
agggcttacc atctggcccc agtgctgcaa tgataccgcg agacccacgc tcaccggctc    3240
cagatttatc agcaataaac cagccagccg aagggccga gcgcagaagt ggtcctgcaa    3300
ctttatccgc ctccatccag tctattaatt gttgccggga agctagagta agtagttcgc    3360
cagttaatag tttgcgcaac gttgttgcca ttgctacagg catcgtggtg tcacgctcgt    3420
cgtttggtat ggcttcattc agctccggtt cccaacgatc aaggcgagtt acatgatccc    3480
ccatgttgtg caaaaaagcg gttagctcct tcggtcctcc gatcgttgtc agaagtaagt    3540
tggccgcagt gttatcactc atggttatgg cagcactgca taattctctt actgtcatgc    3600
catccgtaag atgcttttct gtgactggtg agtactcaac caagtcattc tgagaatagt    3660
gtatgcggcg accgagttgc tcttgcccgg cgtcaatacg ggataatacc gcgccacata    3720
gcagaacttt aaaagtgctc atcattggaa aacgttcttc ggggcgaaaa ctctcaagga    3780
tcttaccgct gttgagatcc agttcgatgt aacccactcg tgcacccaac tgatcttcag    3840
catcttttac tttcaccagc gtttctgggt gagcaaaaac aggaaggcaa aatgccgcaa    3900
aaaagggaat aagggcgaca cggaaatgtt gaatactcat actcttcctt tttcaatatt    3960
attgaagcat ttatcagggt tattgtctca tgagcggata catatttgaa tgtatttaga    4020
aaaataaaca ataggggtt ccgcgcacat ttccccgaaa agtgccacct gacgcgccct    4080
gtagcggcgc attaagcgcg gcgggtgtgg tggttacgcg cagcgtgacc gctacacttg    4140
ccagcgccct agcgcccgct cctttcgctt tcttcccttc ctttctcgcc acgttcgccg    4200
gctttccccg tcaagctcta aatcggggc tcccttagg gttccgattt agtgctttac    4260
ggcacctcga ccccaaaaaa cttgattagg gtgatggttc acgtagtggg ccatcgccct    4320
gatagacggt ttttcgccct ttgacgttgg agtccacgtt ctttaatagt ggactcttgt    4380
tccaaactgg aacaacactc aaccctatct cggtctattc ttttgattta agggattt    4440 tgccgatttc ggcctattgg ttaaaaaatg agctgattta acaaaaattt aacgcgaatt    4500
ttaacaaaat attaacgctt acaatttgcc attcgccatt caggctgcgc aactgttggg    4560
aagggcgatc ggtgcgggcc tcttcgctat tacgccagcc caagctacca tgataagtaa    4620
gtaatattaa ggtacgggag gtacttggag cggccgcaat aaaatatctt tattttcatt    4680
```

```
acatctgtgt gttggttttt tgtgtgaatc gatagtacta acatacgctc tccatcaaaa      4740
caaaacgaaa caaaacaaac tagcaaaata ggctgtcccc agtgcaagtg caggtgccag      4800
aacatttctc tatcgata                                                   4818
```

<210> SEQ ID NO 28
<211> LENGTH: 780
<212> TYPE: DNA
<213> ORGANISM: Mus musculus

<400> SEQUENCE: 28

```
atggccgcgc tgatgcgggt caaggattca tcccgctgcc ttctcctact ggccgcggtg       60
ctgatggtgg agagctcaca gctaggcagc tcgcgggcca aactcaactc catcaagtcc      120
tctctaggag gggagactcc tgctcagtca gccaaccgat ctgcaggcat gaaccaagga      180
ctggctttcg gcggcagtaa gaagggcaaa agcctggggc aggcctaccc ttgcagcagt      240
gataaggaat gtgaagttgg aagatactgc cacagtcccc accaaggatc atcagcctgc      300
atgctctgta ggaggaaaaa gaaacgatgc cacagagatg gcatgtgttg ccctggtacc      360
cgctgcaata atggaatctg catcccagtc actgagagca tcctcacccc acatatccca      420
gctctggatg gcacccggca tagagatcgc aaccatggtc actattccaa ccatgacctg      480
ggatggcaga atctaggaag gccacactcc aagatgcctc atataaaagg acatgaagga      540
gacccatgcc tacggtcatc agactgcatt gatgggtttt gttgtgctcg ccacttctgg      600
accaaaatct gcaaaccagt gctccatcag ggggaagtct gtaccaaaca acgcaagaag      660
ggttcgcacg ggctggagat tttccagagg tgtgactgtg caagggcct gtcctgcaaa      720 gtgtggaaag atgccaccta ctcttccaaa gccagactcc atgtatgcca agatctga       780
```

<210> SEQ ID NO 29
<211> LENGTH: 20
<212> TYPE: DNA
<213> ORGANISM: Artificial Sequence
<220> FEATURE:
<223> OTHER INFORMATION: Mouse DKK2 forward primer

<400> SEQUENCE: 29

```
atggccgcgc tgatgcgggt                                                   20
```

<210> SEQ ID NO 30
<211> LENGTH: 19
<212> TYPE: DNA
<213> ORGANISM: Artificial Sequence
<220> FEATURE:
<223> OTHER INFORMATION: Mouse DKK2 reverse primer

<400> SEQUENCE: 30

```
tcagatcttc tggcataca                                                    19
```

<210> SEQ ID NO 31
<211> LENGTH: 18
<212> TYPE: DNA
<213> ORGANISM: Artificial Sequence
<220> FEATURE:
<223> OTHER INFORMATION: Human DKK2 forward primer

<400> SEQUENCE: 31

```
atggccgcgt tgatgcgg                                                     18
```

<210> SEQ ID NO 32
<211> LENGTH: 18

```
<212> TYPE: DNA
<213> ORGANISM: Artificial Sequence
<220> FEATURE:
<223> OTHER INFORMATION: Human DKK2 reverse primer

<400> SEQUENCE: 32
atggagtctg gctttgga                                                  18
```

DKK2 PROTEIN AND USE THEREOF

CROSS-REFERENCE TO RELATED PATENT APPLICATION

The present application is a Continuation-in-part application of U.S. application Ser. No. 12/302,277, filed Nov. 24, 2008 now U.S. Pat. No. 8,067,387 which is a 371 application of PCT/KR2007/002493, filed May 23, 2007, which claims priority to Korean Application No. 10-2006-0046442, filed May 24, 2006, the contents of which here are incorporated by reference herein in their entirety. The present application also claims benefit of priority to U.S. Provisional Application No. 61/326,509, filed Apr. 21, 2010, the contents of which are incorporated by reference herein in their entirety. The present application also claims the benefit of priority to Korean Application Nos. 10-2011-0022442, filed Mar. 14, 2011, and 10-2011-0022443, filed Mar. 14, 2011, the disclosures of which are incorporated herein by reference in their entirety.

BACKGROUND OF THE INVENTION

1. Field of the Invention

The present invention relates to DKK2, a DKK2-Fc fusion, and a use thereof.

2. Description of the Related Art

DKK2, a repressor protein of Wnt protein, has been reported to act as an inhibiting factor or stimulating factor of signaling pathways of Wnt. DKK2 may be divided into two specific cysteine-rich domains and various lengths of connection regions. Particularly, DKK2, which belongs to the Dickkopf family, highly conserves a cystein-2 region between family members as well as 10 cysteines. It has been reported that DKK2 is closely related with the differentiation of osteoclast.

Angiogenesis is a process by which capillary blood vessels are formed. This process plays an important role in embryogenesis, corpus luteum formation, wound healing, and tumor metastasis. It has been reported that the angiogenesis process is regulated by various stimulating factors and inhibiting factors, for example, growth factor, cytokine, and a lipid metabolism substance. Angiogenesis stimulating factors can be divided into several factors, for example, cell growth inducing factor, cytokine having immune activity, hormone and lipid products, etc. However, the stimulating factors have various problems that arise in clinical use since they act not only on vascular endothelial cells but also on other neighboring cells.

The promotion of angiogenesis may be used for therapeutic purposes. An ischemic disease of an individual may be treated by administering an angiogenic factor to the individual to promote angiogenesis. The angiogenesis factor includes vascular endothelial growth factor (VEGF), fibroblast growth factor (FGF), developmentally regulated endothelial locus-1 (Del-1), hepatocyte growth factor (HGF), platelet-derived endothelial cell growth factor (PD-EGF), angiopoietin, and FGF.

However, the effect of DKK2 or its Fc-fusion on promotion of angiogenesis has been not reported or disclosed.

SUMMARY OF THE INVENTION

The present invention provides a composition and method for promoting angiogenesis.

The present invention also provides a composition and method for promoting filopodia motility in an endothelial cell.

The present invention also provides a composition and method for promoting angiogenic sprouting.

The present invention also provides a composition and method for preventing or treating ischemic disease.

According to an aspect of the present invention, there is provided a composition for promoting angiogenesis, including at least one of DKK2 and a DKK2-Fc fusion protein.

As used herein, the term "DKK2" refers to Dickkopf-2 protein, and is also known as Dickkopf-related protein 2, cysteine-rich secreted protein 2, CRSP2, CRISPY2, or CRSP 2 protein. DKK2 is a protein that in humans is encoded by the DKK2 gene. This gene encodes a protein that is a member of the Dickkopf family. It is known that DKK2, a secreted protein, contains two cysteine-rich regions and is involved in embryonic development through its interactions with a Wnt signaling pathway. In addition, it can act as either a promoter or antagonist of Wnt/beta-catenin signaling, depending on the cellular context and the presence of a co-factor kremen 2. The present inventors have newly found that DKK2 has an activity of promoting angiogenesis. DKK2 may have an amino acid sequence of, for example, SEQ ID NO: 1 or a sequence with its 1-33 sequences removed. The amino acid sequence of SEQ ID NO: 1 is a sequence of human DKK2, corresponds to Genbank accession no. NP_055236, and consists of 259aa. 1-33 is a signal peptide, 77-129 is an N terminal cysteine-rich region, 78-127 and 183-259 are referred to as DKK-type Cys-1 and DKK-type Cys-2 regions, respectively. The DKK2 may be encoded by a gene having a nucleotide sequence of 706-1482 of SEQ ID NO: 2 (Genbank accession no. NM_014421). However, the term "DKK2" used herein is not limited to a human DKK2, but includes DKK2 of other mammals. The DKK2 may be the one isolated from natural source or synthesized by recombinant or chemical method. For example, the above-described DKK2 protein can be prepared by following procedure. The total RNA purified from HUVEC is performed to reverse transcription to obtain complementary DNA; PCR is performed with the obtained complementary DNA as a template and DKK2 primers which are complementary to the complementary DNA2 to obtain amplified DKK2 genes. The DKK2 genes prepared by the above described step are treated with restriction enzyme, cloned into plasmid to obtain the plasmid, which may be cloned and transformed with expression cell lines; the transformed cells are selected and the secreted DKK2 proteins in the medium are purified with column; or DKK2 genes prepared by the above described step are introduced into vector, preferably lentivirus vector, cultured in medium, and the secreted DKK2 proteins in the medium are purified with column.

The DKK2 includes a whole DKK2 or any fragment thereof. The fragment may be any fragment as long as it retains at least one of activities of natural DKK2.

A composition of the present invention includes a fusion protein of DKK2 and an Fc portion of an antibody. The fusion protein may provide a more advantageous dosing schedule to enable therapeutic effects of DKK2 to be extended. That is, DKK2 may be fused with an Fc portion of an antibody to be stabilized and to increase the half-life in the blood. In addition, the fusion protein may be expressed at a level that is higher than the expression of DKK2, and thus it is advantageous for production. The fusion protein may also show an increased solubility and an increased binding to its receptor, compared to natural DKK2. Furthermore, the fusion protein may show angiogenesis promoting effects that are higher than natural DKK2, at a same molar concentration.

Many therapeutic proteins, such as DKK2, have a molecular weight of less than about 40 KDa and are sensitive to a renal clearance by glomerular filtration. It may be difficult for these small proteins to become a complete therapeutic agent. The redesign of a protein to increase the half-life in the blood is medicinally and commercially important. Since proteins are generally injected with a syringe, it is preferable to have a therapeutic protein which may minimize the number of injections of the protein. The effective molecular weight of a protein may be increased by fusion with Fc of an antibody which may aid in purification of the protein. Fc may have any sequence that allows obtained DKK2-Fc protein to have at least one of DKK2 biological activities. Thus, the fusion protein may include any sequence for increasing expression in a host cell, any sequence that is introduced for ease of purification or any restriction enzyme recognition sequence that facilitates the binding of DKK2 to Fc, as long as it retains at least one of biological activities of the DKK2. The DKK2-Fc fusion protein may be one in which the N-terminal of DKK2 is bound to the C-terminal of Fc or the N-terminal of Fc is bound to the C-terminal of DKK2. The binding may be achieved by means of a linker. The DKK2-Fc fusion protein may have an amino acid sequence of SEQ ID NO: 3. 1-9 of SEQ ID NO: 3 is a Pichia expression vector region (pPinka-HC vector region), and the initiator Met is not shown. The 10-325 region is a DKK2 region, the 236-247 region consists of restriction enzyme recognition sites (XhoI, XbaI) and thrombin cleavage sites, and the 248-474 region is a Fc region. Thus, DKK2 may be an amino acid sequence of 10-247 of SEQ ID NO: 3 in the fusion protein. In addition, Fc may have a 248-474 sequence of SEQ ID No: 3. The Fc portion may be an Fc portion of human IgG. The fusion protein may be synthesized in a cell that glycosylates the Fc region at normal glycosylation sites, which usually exist in template antibodies. The fusion protein may be encoded by a nucleotide sequence of SEQ ID NO: 4.

The immunoglobulin Fc region includes an immunoglobulin hinge region and preferably includes at least one immunoglobulin constant heavy region domain, for example, an immunoglobulin constant heavy 2 (CH2) domain, an immunoglobulin constant heavy 3 (CH3) domain, and depending upon the type of immunoglobulin used to generate the Fc region, optionally an immunoglobulin constant heavy region 4 (CH4) domain. Most preferably, the immunoglobulin Fc region lacks at least an immunoglobulin constant heavy 1 (CH1) domain. The immunoglobulin Fc regions may be based on any immunoglobulin class, for example, IgA, IgD, IgE, IgG, and IgM. For example, the immunoglobulin Fc regions may be based on IgG.

In the present specification, angiogenesis refers to a process by which new capillary blood vessels are formed. Angiogenesis includes a process by which new blood vessels grow from pre-existing vessels. Angiogenesis is a normal and important process in wound healing and granulation tissue as well as growth and development. In addition, angiogenesis is a fundamental step in the transition of tumors from a dormant state to a malignant state. Angiogenesis includes sprouting angiogenesis and intussusceptive angiogenesis. Sprouting angiogenesis is characterized by a number of well defined steps. First, biological signals known as angiogenic growth factors activate receptors present on endothelial cells present in pre-existing blood vessels. Second, the activated endothelial cells begin to release enzymes called proteases that degrade a basement membrane to allow endothelial cells to escape from the original (parent) vessel walls. The endothelial cells then proliferate into the surrounding matrix and form solid sprouts connecting neighboring vessels. As sprouts extend toward the source of the angiogenic stimulus, endothelial cells migrate in tandem, using adhesion molecules, the equivalent of cellular grappling hooks, called integrins. These sprouts then form loops to become a full-fledged vessel lumen as cells migrate to the site of angiogenesis. Intussusception, also known as splitting angiogenesis, was first observed in neonatal rats. In this type of vessel formation, the capillary wall extends into the lumen to split a single vessel in two. There are four phases of intussusceptive angiogenesis. First, two opposing capillary walls establish a zone of contact. Second, endothelial cell junctions are reorganized and a vessel bilayer is perforated to allow growth factors and cells to penetrate into the lumen. Third, a core is formed between the two new vessels at the zone of contact and the core is filled with pericytes and myofibroblasts. These cells begin laying collagen fibers into the core to provide an extracellular matrix for growth of the vessel lumen. Finally, the core is fleshed out with no alterations to the basic structure.

In the composition, the promotion may be achieved in vitro or in vivo. The promotion may be an improvement in tissue repair in a subject with an ischemic vascular disease. The ischemic vascular disease may be selected from the group consisting of burn, psoriasis, ulcer, ischemia, myocardial infarction, angina pectoris, cerebral infarction, and cerebral hemorrhage. The subject may be a mammal (e.g. human). For example, the subject may be a human suffering from or susceptible to an ischemic disease. The tissue may a vascular unformed tissue. The term "vascular unformed tissue" disclosed herein comprises newly formed dermal tissue, muscular tissue and connective tissue after the injury caused by ischemic disease in a mammal.

The composition may include a pharmaceutically acceptable carrier. The carrier is meant to include an excipient, a diluent, or an adjuvant. The carrier may be selected from the group consisting of lactose, dextrose, sucrose, sorbitol, mannitol, xylitol erythritol, maltitol, starches, acacia rubber, alginate, gelatin, calcium phosphate, calcium silicate, cellulose, methyl cellulose, polyvinyl pyrrolidone, water, physiological saline solution, buffer such as PBS, methylhydroxy benzoate, propylhydroxy benzoate, talc, magnesium stearate and mineral oil. The composition may include a filler, an anti-agglutinant, a lubricant, a wetting agent, a flavor, an emulsifier, a preservative, etc.

The composition may be formulated by using processes which are known in the art, to provide rapid, continuous or delayed release of the active ingredient after being administered to a subject. The composition may be dissolved in an oil, propylene glycol, or other solvent that is conventionally used for manufacturing injectable solutions. Examples of the carrier include, but are not limited to, physiological saline solution, polyethylene glycol, ethanol, vegetable oil, and isopropyl myristate. For topical application, the composition may be formulated in the form of ointments or creams.

The composition may be prepared in any formulation. The composition may be formulated in an oral dosage form (for example, powder, tablet, capsule, syrup, pill, granule) or a parenteral dosage form (for example, injection). In addition, the composition may be prepared in systemic dosage forms or topical dosage forms.

The composition may include an effective amount of DKK2 and DKK2-Fc fusion. As used herein, the term "effective amount" refers to an amount sufficient to obtain beneficial or desired clinical or biochemical results. As used herein, the effective amount may be an amount sufficient to promote angiogenesis. The effective amount may be also an amount sufficient to improve tissue repair in a subject with an ischemic vascular disease. The effective amount may be also an amount sufficient to promote filopodia motility in an endothelial cell or angiogenic sprouting. The effective amount may vary depending on subjects, formulations, or purposes of use. For example, the composition may include DKK2 and DKK2-Fc fusion protein in an amount of about 0.5 μg to about 2000 mg. DKK2 and DKK2-Fc fusion is used as an active ingredient for treating or preventing ischemic disease. The DKK2 or DKK2-Fc fusion protein may be included in a concentration of 0.1-50% by weight based on the total weight of the composition.

According to another aspect of the present invention, there is provided a composition for promoting filopodia motility in an endothelial cell, including at least one of DKK2 and DKK2-Fc fusion protein. The DKK2, DKK2-Fc fusion protein, and filopodia motility are described as above.

According to another aspect of the present invention, there is provided a composition for promoting angiogenic sprouting, including at least one of DKK2 and DKK2-Fc fusion protein. The DKK2, DKK2-Fc fusion protein, and angiogenic sprouting are described as above.

According to another aspect of the present invention, there is provided a composition for preventing or treating an ischemic vascular disease, including at least one of DKK2 and DKK2-Fc fusion protein.

The ischemic vascular disease may be selected from the group consisting of burn, psoriasis, ulcer, ischemia, myocardial infarction, angina pectoris, cerebral infarction, and cerebral hemorrhage. The composition may include pharmaceutically acceptable carriers in addition to DKK2 and DKK2-Fc fusion protein, which are described as above.

In the composition, the subject may be a mammal, e.g., a human.

The term "treatment" refers to an approach for obtaining beneficial or desired clinical results. For purposes of the present invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission, whether detectable or undetectable. Treatment may also mean prolonging survival as compared to expected survival if not receiving treatment. Treatment may include both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

According to another aspect of the present invention, there is provided a method of promoting angiogenesis in a subject, including administering to the subject a composition for promoting angiogenesis in the subject.

According to another aspect of the present invention, there is provided a method of promoting filopodia motility in a subject by an endothelial cell, including administering to the subject a composition for promoting filopodia motility in the subject by the endothelial cell.

According to another aspect of the present invention, there is provided a method of promoting angiogenic sprouting in a subject, including administering to the subject a composition for promoting angiogenic sprouting.

As described above, according to another aspect of the present invention, there is provided a method of preventing or treating an ischemic vascular disease in a subject, including administering to the subject a composition for preventing or treating an ischemic vascular disease in the subject. The ischemic vascular disease may be selected from the group consisting of a burn, psoriasis, an ulcer, ischemia, myocardial infarction, angina pectoris, cerebral infarction, and cerebral hemorrhage.

In the methods, the materials and compounds mentioned in regard to the composition are the same as those described.

In the methods, the composition may be administered by any administration methods well known in the art. The composition may be administered directly to a subject by any means such as intravenous, intramuscular, oral, transdermal, mucosal, intranasal, intratracheal, or subcutaneous administration. In addition, the composition may be systemically or locally administered. For topical administration, the composition may be formulated in the form of ointments or creams.

The desirable dose of the inventive composition varies depending on the condition and the weight of the subject, severity, drug form, route and period of administration, and may be chosen by those skilled in the art. For example, in order to obtain desirable effects, it mat be administered at the amount ranging from 0.001 to 100 mg/kg, preferably, 0.1 to 100 mg/kg by weight/day of the DKK2 protein or DKK2-Fc fusion. The dose may be administered in single or divided into several times per day.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
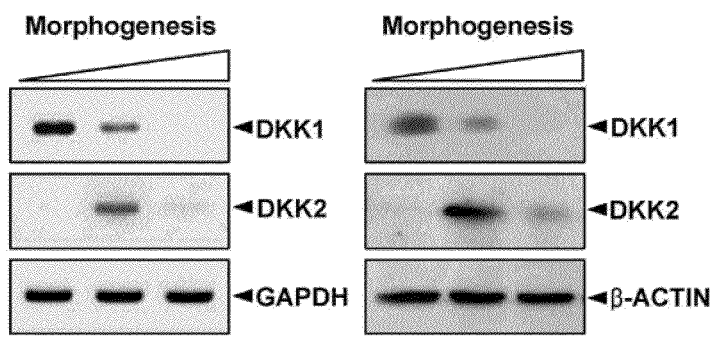
FIG. 1 shows results of mRNA and protein levels of DKK1 and DKK2, measured by RT-PCR (left) and Western blotting (right), respectively, at the same time periods (0.5, 8, and 12 hours) during morphogenesis on Matrigel.

Hereinafter, the present invention will be described in more detail with reference to Examples. However, these Examples are provided only for the purpose of illustrating the present invention and are not intended to limit the scope of the present invention.

The present inventors observed that DKK1 and DKK2, originally known as WNT antagonists that bind to low density lipoprotein (LDL) receptor-related protein (LRP) 5/6 and inhibit β-catenin signaling pathways, are differentially expressed in endothelial cells (ECs) during morphogenetic differentiation on Matrigel.

By employing biochemical and transgenic animal analysis, the present inventors identified that DKK1 and DKK2 play opposite functions in regulating angiogenesis. Surprisingly, DKK2 was found to significantly improve tissue repair with functional neovascularization in ischemic disease models. This study further provides novel mechanistic insights of DKK2 in promoting angiogenic sprouting.

Methods and Materials

Unless otherwise stated, the following methods and materials were used in the following Examples to perform experiments.

(1) Cell Culture

Human umbilical cord vein endothelial cells (HUVECs) were isolated from human umbilical cord veins by collagenase treatment, as conventionally known, and used from passages 2-4 (Jaffe, E. A et al. 1973. J Clin Invest 52:2745-2756). HUVECs were cultured in an EC basal medium (EBM) or EGM™-2 complete medium (Cambrex, Md., USA) with 30% fetal bovine serum (FBS).

(2) In Vitro Morphogenesis on 2D Matrigel and In Vitro Oligonucleotide Microarrays In vitro morphogenesis was assayed as conventionally known (Min, J. K. et al., 2007, Blood 109:1495-1502). Briefly, 800 μl of growth factor-reduced Matrigel (BD Biosciences) was transferred to a 60 mm tissue culture well and polymerized for 30 min at 37° C. HUVECs were plated onto a layer of Matrigel at a density of $1 \times 10^6$ cells/plate and cultured for the indicated times (0.5, 8, and 18 hrs). At each time point, total RNA was isolated and hybridized to the HG-U133A 2.0 microarray (54675 human genes; Affymetrix Santa Clara, Calif., USA). The standard protocol used for sample preparation and microarray processing is available from Affymetrix. The expression data was analyzed using Microarray Suite Version 5.0 (Affymetrix).

(3) EC Proliferation Assay

HUVECs were seeded at a density of $2 \times 10^4$ cells/well in gelatin-coated 24-well plates. After 48 or 72 hrs, cells were washed twice with M199 and incubated for 6 hrs in M199 containing 0.5 μCi/ml of [$^3$H]thymidine (Amersham, Aylesbury, United Kingdom). High molecular weight DNAs were precipitated using 10% trichloroacetic acid at 4° C. for 30 min. After two washes with ice-cold $H_2O$, $^3$H-radioactivity was solubilized in 0.2 N NaOH/0.1° SDS and determined by using a liquid scintillation counter.

(4) In Vivo Matrigel Plug Assay

The Matrigel plug assay was performed as conventionally known. Briefly, 7 week-old C57BL/6 mice (Orient Co. Seoul, Korea) were injected subcutaneously with 0.6 ml of Matrigel containing the indicated amount of DKK2, DKK1, VEGF+ DKK1 and 10 units heparin. The injected Matrigel rapidly formed a single, solid gel plug. After 5 days, the skin of the mouse was easily pulled back to expose the Matrigel plug, which remained intact. Hemoglobin was measured by using the Drabkin method with a Drabkin reagent kit 525 (Sigma, St Louis, Mo.) to quantify blood vessel formation. The concentration of hemoglobin was calculated from a known amount of hemoglobin assayed in parallel. To identify infiltrating ECs, immunohistochemistry was performed with anti-CD-31 antibody (BD Biosciences, San Jose, Calif.).

(5) Mouse Corneal Pocket Assay

Eight week old C57BL6 mice were anesthetized with zoletil 50 (15 mg/kg) and lumpun (5 mg/kg). After 10 min, Alcaine was dropped into their eyes. With a Graefe cataract knife, a micropocket was made in the cornea. Micropellets (0.35×0.35 mm) of sucrose octasulfate-aluminum complex (Sigma S0652) coated with poly-2-hydroxyethyl methacrylate (Sigma p3932) containing 200 ng of VEGF (KOMA Biotech., cat no. K0921632) and 1 μg of DKK2-Fc (self-produced) were implanted into the corneal micropocket. The pellet was positioned 0.6-0.8 mm from the corneal limbus. Tardomyocel-L ointment was applied to the eye after implantation. Eyes were examined 7 days after implantation with a microscope. Cryosections were stained with anti-CD31 (BD Pharmingen™) and anti-NG2 (Millipore) antibodies.

(6) Aortic Ring Assay

Aortas were harvested from 6-8 week-old C57BL/6 wild type (WT) and DKK2 transgenic (Tg) mice. Plates (48-well) were coated with 100 μl of Matrigel, and after it had gelled, rings were placed in the wells and sealed in place with an overlay of 40 μl of Matrigel. EGM were added to the wells in a final volume of 200 μl of human endothelial serum-free medium (Invitrogen). On day 5, cells were fixed and stained with isolectin B4. The assays were scored, double blind, from 0 (least positive) to 5 (most positive). Each data point was assayed six times. Endothelial sprouts were time-lapse imaged by using an Olympus IX81-ZDC inverted fluorescence microscope.

(7) Analysis of Mouse Retinal Vasculature

The vascular pattern of dissected mouse retina was analyzed according to the method modified from the conventional report (Gerhardt, H. et al. 2003. *J Cell Biol* 161:1163-1177), Mice were killed by ketarnine injection and their eyes were enucleated in PBS. The eyes were fixed in 4% PFA-PBS (pH 7,4) for 1 hr at 4° C. Retinas were dissected as conventionally known (Kang, Y. et al., *PLoS One* 4:e4275), postfixed in 70% ethanol overnight at 4° C.; washed with PBS and permeabilized with PBS containing 1% Triton-X-100 for 1 hr. Retinas were then incubated in blocking solution for 4 hrs at 37° C., followed by overnight incubation in Alexa488-conjugated Isolectin GS-IB4 solution (Molecular Probes) at 4° C. After five washes in PBS containing 1% Triton-X-100, the retinas were flat mounted on slides using a fluorescent mounting medium. The flat mounted retinas were analyzed by fluorescence microscopy by using an Olympus IX81-ZDC inverted fluorescence microscope and a confocal fluorescent microscope, Carl Zeiss LSM 510 META.

(8) Cryosection Immunofluorescence Staining

Tissue was fixed in 4% PFA-PBS (pH 7.4) overnight at 4° C. and rinsed with PBS at room temperature. The tissue was then incubated in 15% sucrose solution overnight at 4° C., and then transferred to 30% sucrose at 4° C. until the tissue sank. All fixation, rinsing, and incubation were done gently. Tissue was infiltrated in an optimal cutting temperature (O.C.T.) embedding medium (Tissue Tek) for 0.5 hr at room temperature before freezing. The tissue was transferred to an embedding mold, which was filled with O.C.T. The mold was cooled with liquid nitrogen. After the material had frozen, the tissue was wrapped in aluminum foil and stored at −70° C., Sections (8-50 μm thick) were cut at −20° C., and slides were stored at −70° C. until needed. Sections were prefixed in acetone for 0.5 hr at −70° C. and then dried briefly until the acetone was removed. The O.C.T. was removed with water. Sections were incubated in blocking solution for 4 hrs at 37° C. or overnight at 4° C., followed by overnight incubation in a primary antibody at 4° C. After five washes in 0.3% Triton-X-100 in PBS for 15 min each wash, the sections were incubated in a secondary antibody overnight at 4° C., Before washing, the sections were treated with DAPI (1 g/Ml) and then washed five more times 0.3% Triton-X-100 in PBS for 15 min each wash. All antibodies were dissolved in an antibody diluent (Dako). Sections were analyzed by fluorescence microscopy by using an Olympus IX81-ZDC inverted fluorescence microscope or a confocal microscope (Carl Zeiss, LSM 510 META).

(9) Murine Hindlimb Ischemic Model

BalB/cAnNCriBgi-nu nude male mice were obtained from Charles River Japan Inc, (Yokohama, Japan). All mice were 7-8 weeks (15-20 g) of age at the time of study. Hindlimb ischemia was induced by ligation and excision of the right femoral artery and vein under ketamine-xylazine anesthesia. For angiogenic potential studies, mice were divided into three groups after induction of ischemia. Mice received intramuscular injection of PBS (20 μl with 0.9% NaCl) alone as a control, saline solution containing DKK2-Fc (20 μl of 600 ng/μl), or saline solution containing vascular endothelial growth factor (VEGF)(20 μl of 150 ng/μl).

(10) NIR Fluorescence Imaging

The present inventors used customized optical systems for NIR fluorescence imaging, as previously described by Kang et al *PLoS One* 4:e4275. Briefly, this system employs a CCD digital camera (PIXIS 1024; Princeton instruments, Princeton, N. J., USA) with a custom-made 830-nm bandpass filter (Asahi Spectra USA, Torrance, Calif., USA) and 760-nm light-emitting diode arrays (SMC760; Marubeni America, Sunnyvale, Calif., USA). For time-series ICG imaging, mice under ketamine-xylazine anesthesia were injected with an intravenous bolus of ICG (0.1 Ml of 400 mM/l; Sigma, St. Louis, Mo., USA) into their tail veins. ICG fluorescence images were obtained in a dark room for 10 min at 1 sec intervals immediately after injection. After the serial imaging, customized and computerized programs were used to obtain perfusion maps and necrosis probabilities.

(11) Myocardial Infarction Model and Experimental Procedure

Myocardial Infarction (MI) was induced in 8-week-old Sprague-Dawley male rats (Song, H. et al., Stem Cells 25:1431-1438). The rats were anesthetized with ketamine (10 mg/kg) and xylazine (5 mg/kg), and surgical occlusion of their left anterior descending coronary arteries was performed with a 6-0 silk suture (Johnson & Johnson, Belgium).

After 60 min of occlusion, the ligated myocardium was reperfused, and 3 μg of DKK2-Fc protein was injected into three sites from the injured region to the border using a Hamilton syringe (Hamilton Co., Reno, Nev., USA) with a 30-gauge needle. Throughout the operation, the rats were ventilated with 95% $O_2$ and 5% $CO_2$ using a Harvard ventilator. Six animals per group were used for morphologic analysis 1 week after the operation. For functional studies, the present inventors performed echocardiography at 3 weeks. To determine infarct size, the hearts were removed and perfused with 1% 2,3,5-triphenyltetrazolium chloride (TTC, Sigma, St. Louis, Mo., USA) solution, pH 7.4, at 37° C. for 20 min, and then fixed in 10% PBS-buffered formalin overnight at 2-8° C.

(12) Histology and Immunohistochemistry of the Rat Myocardiac Infarction Model

A heart was excised, fixed with 10% PBS-buffered formalin for 24 hrs, and embedded in paraffin. Sections (5 μm thick) were mounted on gelatin-coated glass slides to allow the use of different stains on different sections. After deparaffinization and rehydration, the tissue sections were stained with Masson's trichrome for analysis of fibrosis. For histological analysis, an R.T.U. VECTASTATIN Universal Quick kit (Vector Laboratories, Burlingame, Calif., USA) was used for paraffin sections. The sections were deparaffinized, rehydrated, and rinsed with PBS. Antigen retrieval was performed by microwaving for 10 min in 10 mM sodium citrate (pH 6.0). The sections were incubated in 3% $H_2O_2$ to quench endogenous peroxidase activity. The sections were blocked in 2.5% normal horse serum and incubated in a primary antibody (CD31). A biotinylated pan-specific universal secondary antibody and a streptavidin/peroxidase complex reagent were used for the heart sections, which were stained with an antibody by using a DAB substrate kit (Vector Laboratories). Sections were counterstained with 1% methyl green and dehydrated in 100% N-butanol, ethanol, and xylene before mounting in VectaMount Medium (Vector Laboratories).

(13) TUNEL Assay of Tissue

The terminal deoxynucleotidyl transferase dUTP nick and labeling (TUNEL) assay is a method of detecting DNA fragmentation by marking the end of nucleic acid. The TUNEL assay was performed according to the manufacturer's instructions (Chemicon International Inc. Temecula, Calif., USA). A positive control sample was prepared from a normal heart section by treating the section with DNase I (10 U/Ml, 10 min at room temperature). Sections were pretreated with 3.0% $H_2O_2$, subjected to TdT enzyme for 37° C. for 1 hr, and incubated in digoxigenin-conjugated nucleotide substrate at 37° C. for 30 min. Nuclei exhibiting DNA fragmentation were visualized by adding 3,3-diaminobenzidine (DAB) (Vector Laboratories, Burlingame, Calif., http://www.vectorlab.com) for 5 min. Finally, the sections were counterstained with methyl green and analyzed by light microscopy. For each group, six sections were prepared, and 10 different regions were observed per section (×200).

(14) Echocardiography

Transthoracic echocardiographic studies were performed by an experienced cardiologist blinded to group assignments, using a GE Vivid Seven ultrasound machine (GE Medical System, Salt Lake City, Utah, USA) with a 10.0 MHz transducer. Rats received general anesthesia and were placed in a left lateral decubitus position. The echo transducer was placed on a left hemithorax, and short axis views were recorded. Two-dimensional images were obtained at midpapillary level (Song, H. et al. Stem Cells 25:1431-1438). M-mode tracing of LV contraction was obtained at the same level as the short-axis view. LV end diastolic diameter (LVEDD) and LV end systolic diameter (LVESD) were measured with M-mode tracing. Percent fractional shortening (% FS) was calculated using $[(LVEDD-LVESD)/LVEDD]\times100$ (%). LV end diastolic volume (LVEDV) was calculated as $7.0\times LVEDD^3/(2.4+LVEDD)$, LV end systolic volume (LVESV) as $7.0\times LVESD^3/(2.4+LVESD)$, and LV ejection fraction (EF) as $EF(\%)=(LVEDV-LVESV)/LVEDV\times100$. Two images per view were obtained, and each parameter was measured from three consecutive beats per image. Six values of each parameter were obtained and averaged. Echocardiograms were stored digitally and analyzed with EchoPAC with custom 2-D strain rate imaging software. More than three images were obtained in the short axis view, and the parameters were measured from three consecutive beats in each image.

(15) RT-PCR Analysis

Total RNA was isolated from HUVECs using a TRIzol reagent kit. Different amounts of total RNA (0.5-5 μg) were amplified with RT-PCR, and the correlation between the amount of RNA used and the level of PCR products obtained from target mRNAs and the internal standard (GAPDH) mRNA was examined. Briefly, cDNA was synthesized from target RNA using 200 U of reverse transcriptase and 500 ng of oligo (dT) primer in 50 mM Tris-HCl (pH 8.3), 75 mM KCl, 3 mM $MgCl_2$, 10 mM DTT, and 1 mM dNTPs at 42° C. for 1 hr. The reaction was stopped by heating at 70° C. for 15 min. A total of 1 μl of the cDNA mixture was then used for enzymatic amplification. PCR was performed in 50 mM KCl, 10 mM Tris-HCl (pH 8.3), 1.5 mM $MgCl_2$, 0.2 mM dNTPs, 2.5 U of Taq DNA polymerase (Promega), and 0.1 μM of each primer for target genes in a DNA thermal cycler (model PTC-200; MJ Research) under the following conditions: denaturation at 94° C. for 5 min for the first cycle and for 30 sec starting from the second cycle, annealing at 55° C. for 30 sec, and extension at 72° C. for 30 sec for 25 cycles. Final extension was at 72° C. for 10 min.

The following primer pairs were designed for RT-PCR and synthesized by Bioneer Inc. (Seoul, Korea) (Table 1).

TABLE 1

| Target | Primer pair name | SEQ ID NO: |
| --- | --- | --- |
| mDKK2 | mDKK2_A | 5 and 6 |
| mDKK2 | mDKK2_B | 7 and 8 |
| mGAPDH | mGAPDH | 9 and 10 |
| DKK1 | DKK1 | 11 and 12 |
| DKK2 | DKK2 | 13 and 14 |
| KREMEN2 | KREMEN2 | 15 and 16 |
| LRP6 | LRP6 | 17 and 18 |
| LRP5 | LRP5 | 19 and 20 |
| Adenomatous Polyposis Coli (APC) | APC | 21 and 22 |
| Asef2 | Asef2 | 23 and 24 |
| GAPDH | GAPDH | 25 and 26 |

(16) Cdc42 Assay

Cdc42 activity was measured with a CDC42 activation kit (Upstate, Calif.) according to the manufacturer's instructions (Upstate Biotechnology, Inc.). HUVECs were washed once with ice-cold PBS and lysed with lysis buffer containing 25 mM Hepes, pH 7.5, 150 mM NaCl, 1% Igepal CA-630, 10 mM $MgCl_2$, 1 mM EDTA, 10% glycerol, 1 mM $Na_3VO_4$, 10 μg/Ml aprotinin, 10 μg/Ml leupeptin, and 25 mM NaF for 15 min at 4° C. Insoluble materials were removed by centrifugation.

5 μg of PAK1-agarose beads, which specifically bind to activated Cdc42, were added to the cell lysates and incubated for 1 hr at 4° C. Agarose beads were washed with lysis buffer three times and boiled in 2× Laemmli sample buffer. Samples were resolved with SDS-PAGE and immunoblotted with an anti-Cdc42 antibody.

(17) Animal Studies

All mice were maintained in a laminar airflow cabinet under specific pathogen-free conditions. All facilities are approved by AAALAC (Association of Assessment and Accreditation of Laboratory Animal Care), and all animal experiments were conducted under the institutional guidelines established for the Animal Core Facility at Yonsei University College of Medicine.

(18) Statistical Analysis

Data is presented as mean±SD or ±SE. Statistical comparisons between groups were performed using one-way ANOVA followed by Student t test.

EXAMPLE 1

Expression Aspect of DKK1 and DKK2 During Endothelial Morphogenesis

To identify factors potentially working at a sprouting front, the present inventors employed gene microarrays to isolate genes that reversibly change their expression during in vitro proliferation and morphogenesis of ECs. The gene microarrays used were HG-U133A 2.0 microarrays (54,675 genes; Affymetrix Santa Clara, Calif., USA).

FIGS. 1-4 are views showing that DKK1 and DKK2 are reciprocally expressed during endothelial morphogenesis and distinctively regulate angiogenesis in vitro.

FIG. 1 is a group of views illustrating results of mRNA and protein levels of DKK1 and DKK2, measured by RT-PCR (left) and Western blotting (right), respectively, at the same time periods (0.5, 8, and 12 hrs) during morphogenesis on Matrigel.

Figure 2:
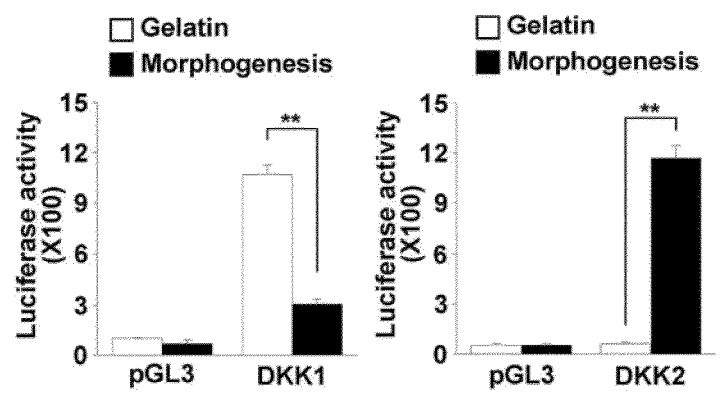
FIG. 2 shows graphs illustrating results of human DKK1 and DKK2 promoter activities measured by luciferase reporter assay.
Figure 40:
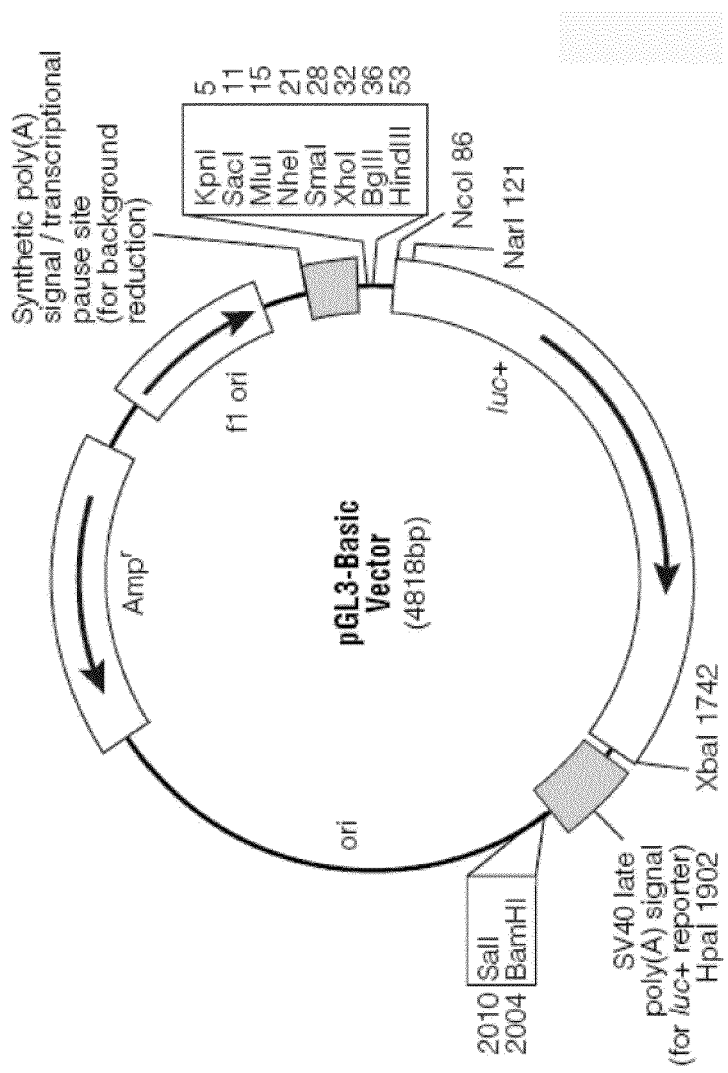
FIG. 40 is a view illustrating a map of a pGL3-Basic vector.

FIG. 2 is a group of graphs illustrating results of human DKK1 and DKK2 promoter activities measured by luciferase reporter assay. In the luciferase reporter assay, luciferase activity represents the activities of DKK1 promoter and DKK2 promoters. HUVECs cultured on a gelatin-coated plate were transfected with a pGL3 luciferase reporter vector, and the transfected cells were transferred to the gelatin-coated plate (gelatin) and Matrigel-coated plate (morphogenesis) at 6 hrs post-transfection. In FIG. 2, pGL3 refers to a HUVEC transfected into pGL3 as a control vector. Here, pGL3 is a pGL3-Basic Vector (Promega Corporation, Madison, Wis., USA) commercially available and a vector in which DKK1 and DKK2 promoters are not introduced. FIG. 40 is a view illustrating a map of pGL3-Basic vector. SEQ ID NO: 27 represents a nucleotide sequence of the pGL3-Basic Vector. DKK1 and DKK2 represent HUVECs transfected with vectors in which pGL3 DKK1 promoter and DKK2 promoter are introduced into the upstream of a luc gene of the pGL3-Basic Vector. Data is average ±SD (**p<0.01).

Figure 3:
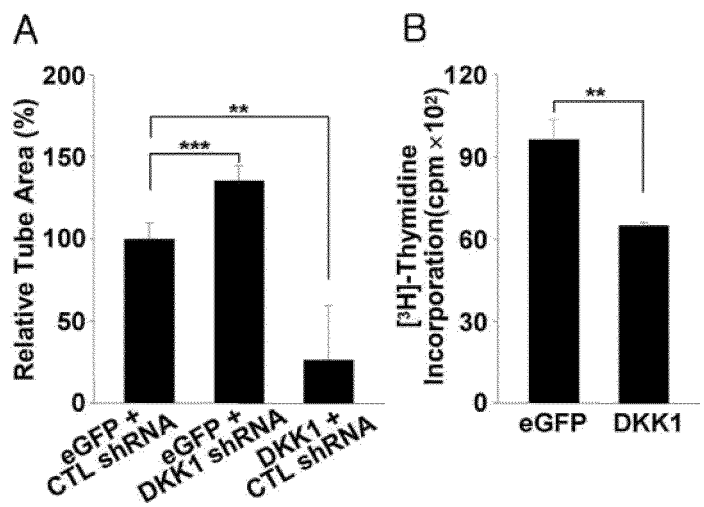
FIG. 3 shows graphs illustrating effects of DKK1 on tube formation by human umbilical vein endothelial cell (HUVEC) (A) and on HUVEC proliferation (B)
Figure 39:
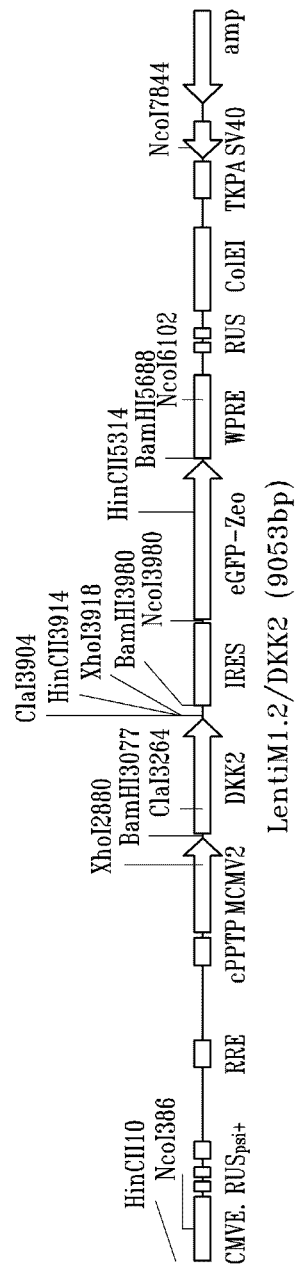
FIG. 39 is a view illustrating a map of a lentiviral vector.

FIG. 3 is a group of graphs illustrating effects of DKK1 on tube formation by HUVEC (A) and on HUVEC proliferation (B). In FIG. 3, HUVECs stably expressing eGFP plus control (CTL) shRNA, eGFP plus DKK1 shRNA, or DKK1 plus control (CTL) shRNA were established with lentivirus (Macrogen Inc, Korea). Each gene was introduced via each lentiviral vector. Each lentiviral vector employed a structure in which each gene was introduced in pLentiM1.2/DKK2 (9053 bp) with a map disclosed in FIG. 39 at a region corresponding to the DKK2 gene locus and thus replacing the DKK2 gene locus. A small hairpin RNA (shRNA) used herein is a sequence of RNA making a tight hairpin turn used to silence gene expression via RNA interference. The shRNA hairpin is cleaved by cellular machinery into siRNA, which is then bound to a RNA-induced silencing complex (RISC). This complex binds to and cleaves mRNAs. The control shRNA employed a sequence which is not complementary to a transcriptome of DKK1-, eGFP or other genes as a random sequence, and DKK1 shRNA has a sequence which is complementary to mRNA encoded from a DKK1 gene. Therefore, HUVECs stably expressing DKK1 shRNA are cells in which the expression of DKK1 gene is silenced. Stable transfectants were plated on Matrigel-coated plates at a density of $1.5 \times 10^5$ cells/well and incubated for 18 hrs. Capillary-like networks which were completely differentiated into tube-like structures were quantified with Image-Pro Plus software. In FIG. 3B, proliferative indices of HUVECs transfected with eGFP or DKK1 were assessed by [$^3$H] thymidine incorporation assay.

Figure 4:
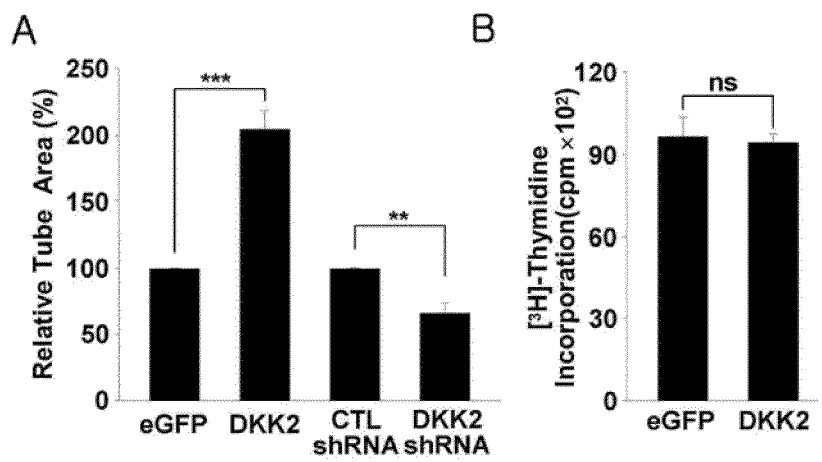
FIG. 4 shows graphs illustrating effects of DKK2 on tube formation by HUVEC (A) and on HUVEC proliferation (B)

FIG. 4 is a group of graphs illustrating effects of DKK2 on tube formation by HUVEC (A) and on HUVEC proliferation (B). In FIG. 4A, HUVECs stably expressing eGFP, DKK2, control (CTL) shRNA, and DKK2 shRNA were established with lentivirus (Macrogen Inc, Korea). The lentiviral vector employed a similar structure, except for DKK2 in pLentiM1.2/DKK2 (9053 bp), a map disclosed in FIG. 39. The small hairpin RNA (shRNA) used herein is a sequence of RNA making a tight hairpin turn used to silence gene expression via RNA interference. The shRNA hairpin is cleaved by the cellular machinery into siRNA, which is then bound to the RNA-induced silencing complex (RISC). This complex binds to and cleaves mRNAs. The control shRNA employed a sequence which is not complementary to a transcriptome of DKK2-, eGFP or other genes as a random sequence, and DKK2 shRNA has a sequence which is complementary to mRNA encoded from a DKK2 gene. Therefore, HUVECs stably expressing DKK2 shRNA are cells in which the expression of DKK2 gene is silenced. Stable transfectants were plated on Matrigel-coated plates at a density of $1.5 \times 10^5$ cells/well and incubated for 18 hrs. Capillary-like networks which were completely differentiated into tube-like structures were quantified with Image-Pro Plus software. In FIG. 4B, proliferative indices of HUVECs transfected with eGFP or DKK2 were assessed by [$^3$H] thymidine incorporation assay. Data is mean±SD (p<0.01, *p<0.001, ns; not significant).

As shown in FIGS. 1-4, interestingly, a reciprocal change in the expression of Dickkopf family members, DKK1 and DKK2, was found during morphogenesis of HUVECs. DKK1 was rapidly downregulated upon induction of morphogenesis on 2D Matrigel, whereas DKK2 was up-regulated during this process.

Figure 5:
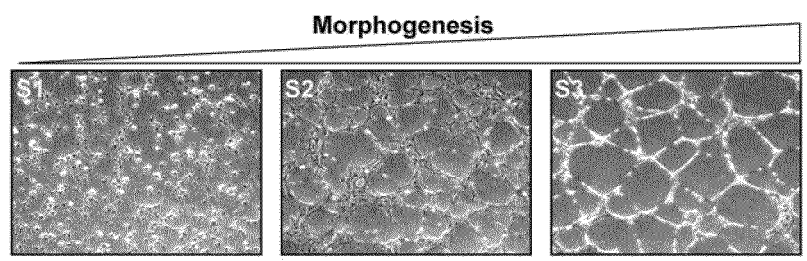
FIGS. 5-7 are photographs illustrating reversible changes in expression of DKK1 and DKK2 during in vitro morphogenesis.
Figure 6:
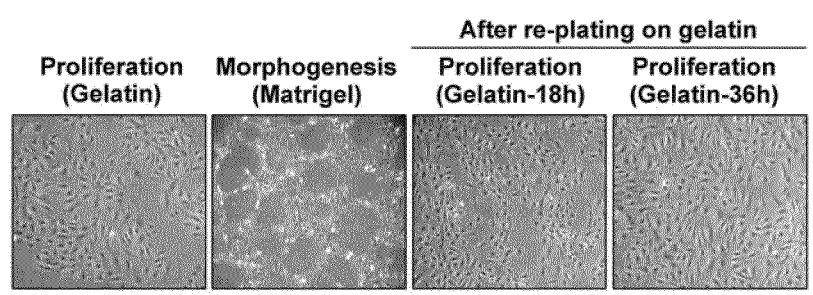
Figure 7:
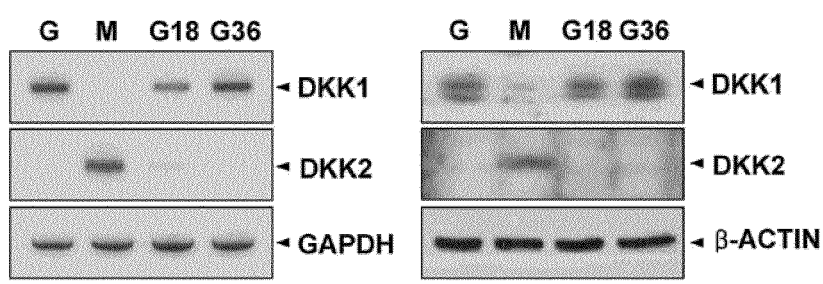

FIGS. 5-7 are photographs illustrating reversible changes in expression of DKK1 and DKK2 during in vitro morphogenesis.

FIG. 5 is a group of photographs illustrating a process of in vitro endothelial morphogenesis of HUVECs on Matrigel. Microphotographs were obtained at different time points (S1: 0.5 hr, S2: 8 hrs, and S3: 18 hrs).

In FIG. 6, HUVECs proliferating on gelatin were plated on Matrigel-coated plates and incubated for 8 hrs. Subsequently, the cells were re-plated on gelatin-coated plates and allowed to proliferate for the indicated times (18 and 36 hrs).

FIG. 7 is a group of photographs illustrating results of mRNA and protein levels of DKK1 and DKK2, measured by RT-PCR (left) and Western blotting (right), respectively, during experimental processes in FIGS. 5 and 6. G: gelatin, M: Matrigel, G18: 18 hrs after being re-plated on gelatin, and G36: 36 hrs after being re-plated on gelatin.

As shown in FIGS. 5-7, the reciprocal changes in expression of DKK1 and DKK2 represent that they were reversibly and transcriptionally controlled during a morphogenesis state on Matrigel and a proliferation state on gelatin.

Figure 8:
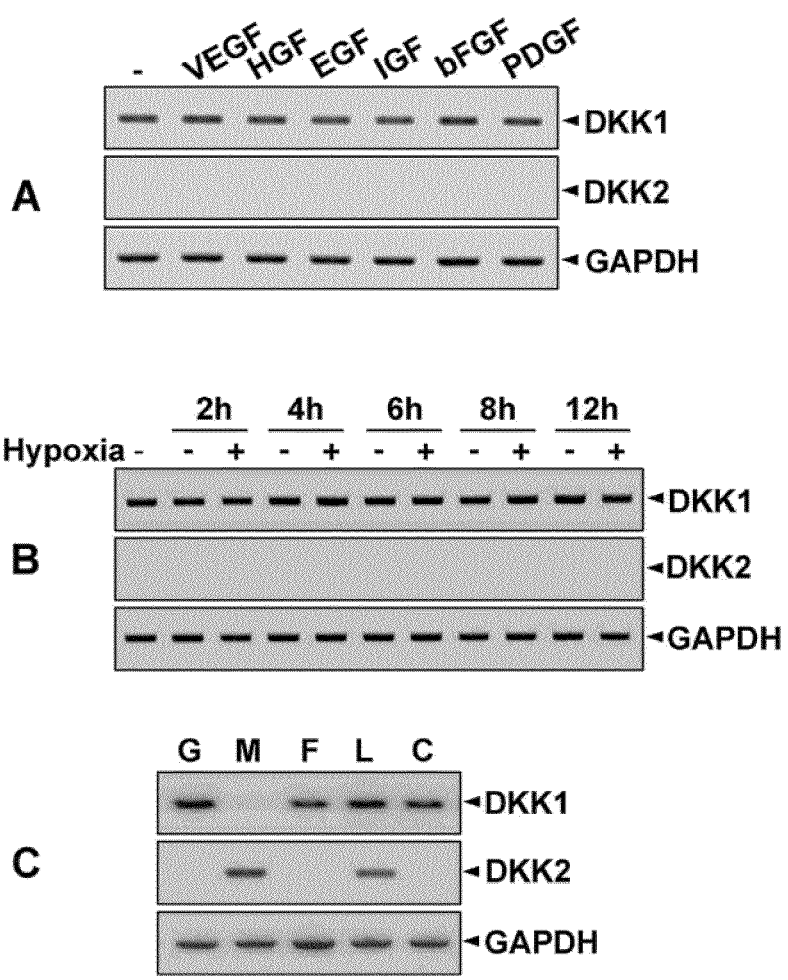
FIGS. 8-10 are photographs illustrating effects of angiogenic mediators and microenvironments on the DKK1 and DKK2 expression.
Figure 9:
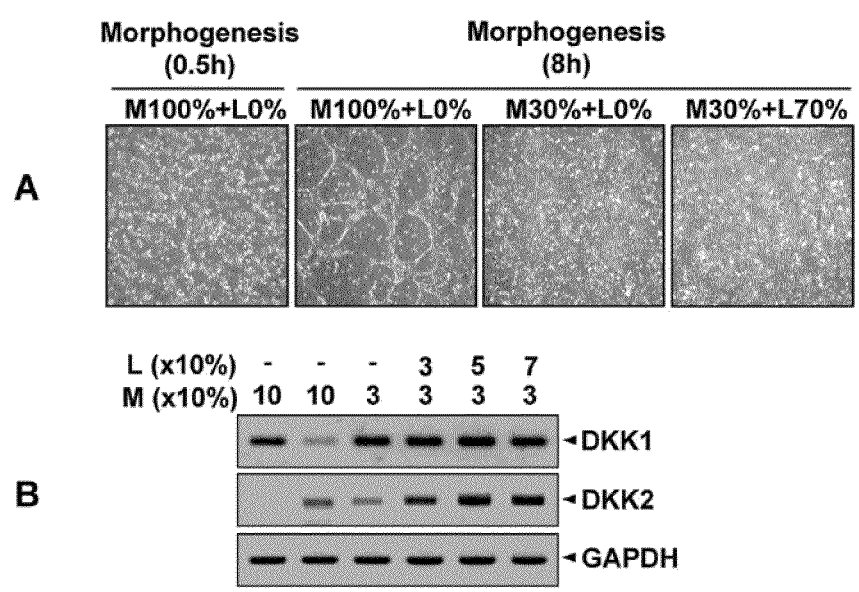
Figure 10:
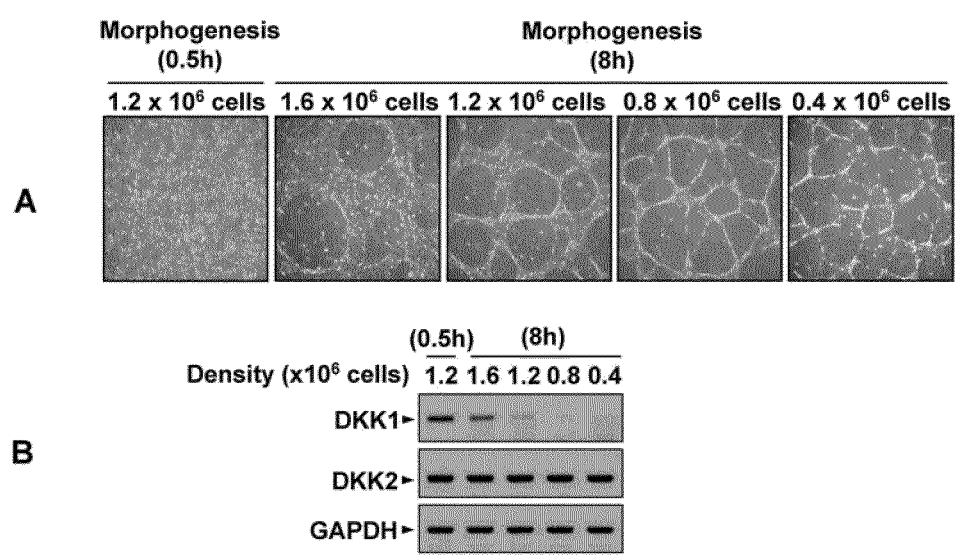

The present inventors further investigated the regulation of DKK1 and DKK2 gene expression. FIGS. 8-10 are photographs illustrating effects of angiogenic mediators and microenvironments on the DKK1 and DKK2 expression.

FIG. 8 is a group of photographs illustrating effects of angiogenic mediators (VEGF, HGF, EGF, IFG, bFGF, and PDGF)(A), hypoxia conditions (B), and microenvironements (gelatin, Matrigel, fibronectin, laminin, or collagen) (C) on the DKK1 and DKK2 expression. In FIG. 8A, HUVECs were stimulated with VEGF (20 ng/ml), HGF (20 ng/ml), EGF (20 ng/ml), IGF (50 ng/ml), bFGF (20 ng/ml), or PDGF (50 ng/ml) for 8 hrs. In FIG. 8B, HUVECs were incubated for the indicated times under hypoxia or normoxia conditions. In FIG. 8C, HUVECs were plated on gelatin (G)-, Matrigel (M)-, fibronectin (F)—, laminin (L)-, or collagen (C)-coated plates and incubated for 8 hrs. mRNA levels of DKK1 and DKK2 were measured by RT-PCR.

FIG. 9 is a group of photographs illustrating effects of laminin on the DKK1 and DKK2 expression. In FIG. 9, HUVECs were plated on Matrigel (M)- or Matrigel plus laminin (L)-mixtures coated plates at a density of $1 \times 10^6$ cells/well and incubated for 0.5 or 8 hrs. FIG. 9A represents a group of microphotographs taken, and FIG. 9B represents mRNA levels of DKK1 and DKK2 measured by RT-PCR.

FIG. 10 is a group of photographs illustrating effects of cell density of HUVECs on the DKK1 and DKK2 expression on Matrigel-coated plates. In FIG. 10, HUVECs were plated on Matrigel-coated plates at the indicated densities and incubated for 0.5 or 8 hrs. FIG. 10A represents a group of microphotographs, and FIG. 10B represents mRNA levels of DKK1 and DKK2 measured by RT-PCR.

As shown in FIGS. 8-10, none of the angiogenic factors tested nor the hypoxic condition had an effect on DKK1 and DKK2 expression (FIGS. 8A and 8B). However, DKK2 was sufficiently induced by EC recognition of laminin, a major component of Matrigel, and did not require morphological changes of ECs (FIGS. 8A, 9A, and 9B). However, down-regulation of DKK1 was correlated with the induction of morphological changes in ECs (FIGS. 10A and 10B) and it was not significantly affected by the recognition of specific extracellular matrix (ECM) components (FIG. 8C).

EXAMPLE 2

Distinct Roles of DKK1 and DKK2 During In Vitro Angiogenesis

In the present Example, the present inventors determined the roles of DKK1 and DKK2 in angiogenesis in vitro.

Figure 11:
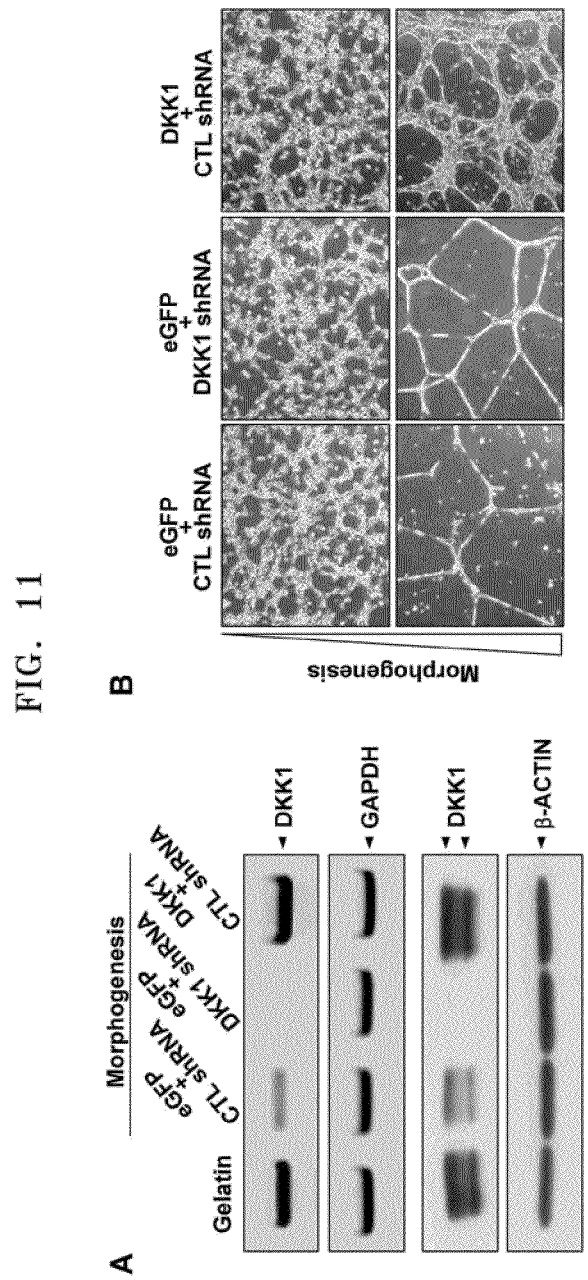
FIG. 11 is a group of photographs illustrating roles of DKK1 during in vitro morphogenesis.

FIG. 11 is a group of photographs illustrating roles of DKK1 during in vitro morphogenesis. In FIG. 11, HUVECs stably expressing eGFP plus control (CTL) shRNA, eGFP plus DKK1 shRNA, or DKK1 plus control (CTL) shRNA were established with lentivirus. Here, DKK1 shRNA and control shRNA were described in the same manner as in FIG. 3. FIG. 11A is a group of photographs illustrating results of mRNA and protein levels of DKK1 measured by RT-PCR (upper portion) and Western blotting (lower portion). FIG. 11A shows that stable transfectants were plated on gelatin-coated plates (Gelatin) or Matrigel-coated plates (Morphogenesis) at a density of $1.5 \times 10^5$ cells/well and incubated for 18 hrs. FIG. 11B is a group of microphotographs showing that stable transfectants were plated on Matrigel-coated plates at a density of $1.5 \times 10^5$ cells/well and incubated for 18 hrs.

Figure 12:
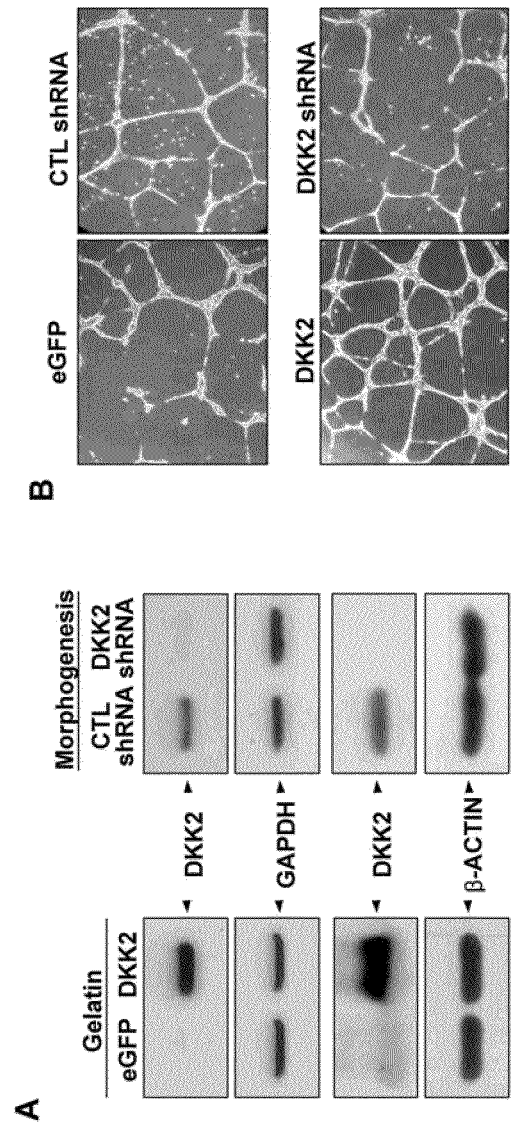
FIG. 12 is a group of photographs illustrating roles of DKK2 during in vitro morphogenesis.

FIG. 12 is a group of photographs illustrating roles of DKK2 during in vitro morphogenesis. In FIG. 12, HUVECs stably expressing eGFP, DKK2, control (CTL) shRNA, or DKK2 shRNA were established with lentivirus. Here, DKK2 shRNA and control shRNA were described in the same manner as in FIG. 4. FIG. 12A is a group of photographs illustrating results of mRNA and protein levels of DKK2 measured by RT-PCR (upper portion) and Western blotting (lower portion). FIG. 12A shows that stable transfectants were plated on gelatin-coated plates (Gelatin) or Matrigel-coated plates (Morphogenesis) at a density of $1.5 \times 10^5$ cells/well and incubated for 18 hrs. FIG. 12B is a group of microphotographs showing that stable transfectants were plated on Matrigel-coated plates at a density of $1.5 \times 10^5$ cells/well and incubated for 18 hrs.

Figure 13:
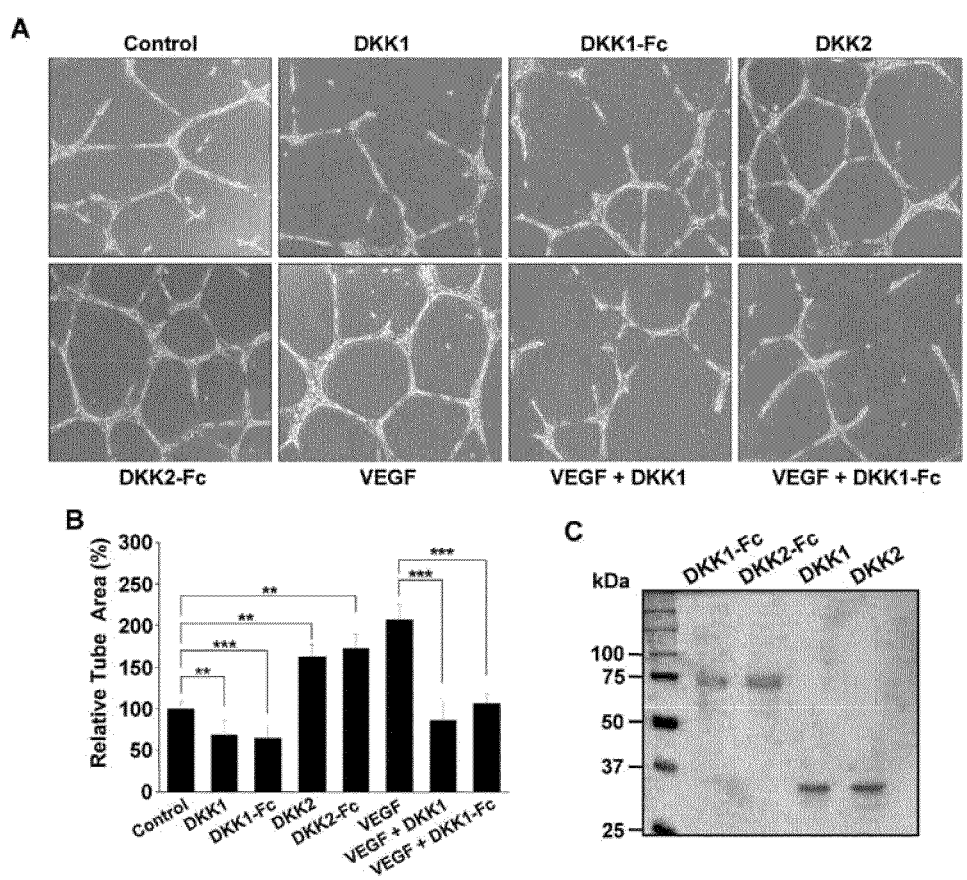
FIG. 13 is a group of views illustrating effects of recombinant DKK1, DKK2, and Fc fusion thereof on the formation of an endothelial cell (EC) tube-like structure.

FIG. 13 is a group of views illustrating effects of recombinant DKK1, DKK2, and Fc fusion thereof on the formation of EC tube-like structures. In FIGS. 13A and 13B, HUVECs ($5 \times 10^5$) were incubated with recombinant native DKK1 (100 ng/ml), Fc-fusion (DKK1-Fc)(100 ng/ml), recombinant native DKK2 (100 ng/ml), Fc-fusion (DKK2-Fc) of SEQ ID NO: 3, VEGF (20 ng/ml), recombinant native DKK1 (100 ng/ml) plus VEGF (20 ng/ml) or recombinant native DKK1 (100 ng/ml) plus VEGF (20 ng/ml) on Matrigel. FIG. 13A is a group of microphotographs illustrating representative endothelial tubes after 18 hrs of incubation. FIG. 13B is a graph showing that capillary-like networks which were completely differentiated into tube-like structures were quantified with Image-Pro Plus software. Data is mean±SD (p<0.01, *p<0.001). FIG. 13C is a photograph showing that recombinant native (DKK1, DKK2) or Fc-fusion (DKK1-Fc, DKK2-Fc) were separated by SDS-PAGE and stained with Coomassie blue.

Figure 14:
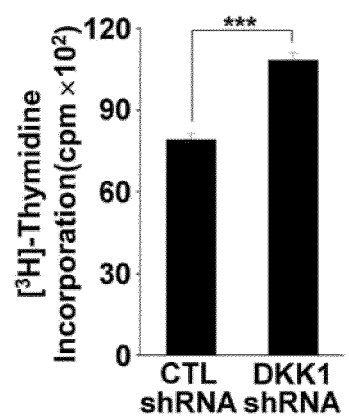
FIG. 14 is a graph illustrating effects of knock-down of DKK1 on HUVEC proliferation on a gelatin-coated plate.

FIG. 14 is a graph illustrating effects of knock-down of DKK1 on HUVEC proliferation on a gelatin-coated plate. In FIG. 14, proliferative indices of HUVECs stably transfected with control or DKK1-specific shRNA were assessed by [$^3$H] Thymidine incorporation assay.

As described above, sustained expression of DKK1 during in vitro morphogenesis of HUVECs or treatment with recombinant DKK1 protein suppressed the formation of EC tube-like structures on 2D Matrigel (FIGS. 3A, 11, and 13). In contrast, overexpression of DKK2 or treatment with recombinant DKK2 protein enhanced the integrity of EC tube-like structures, while knockdown of DKK2 during morphogenesis inhibited the integrity. In addition, although DKK2 and Fc-fusion, for example, DKK2 and Fc-fusion having an amino acid sequence of SEQ ID NO: 3 was used at a weight equivalent to that of DKK2, i.e., at a molar concentration smaller than that of DKK2, a tube-like structure similar to the case when native DKK2 is used was unexpectedly formed (FIGS. 13A and 13B).

Interestingly, EC proliferation on gelatin also was significantly inhibited by DKK1 overexpression, and increased by DKK1 shRNA transfection (FIGS. 3B and 14). Overexpression of DKK2 had no significant effect on EC proliferation on gelatin (FIG. 4B).

These results suggest that DKK1 and DKK2 perform opposite functions during angiogenesis in vitro.

EXAMPLE 3

In Vivo Promotion of Angiogenesis by DKK2

The present inventors identified that DKK is a proangiogenic factor in vivo.

To evaluate the effects of DKK1 and DKK2 on angiogenesis in vivo, the present inventors employed the Matrigel implant assay in mice (See "(4) In vivo Matrigel Plug assay" and "(5) Mouse corneal pocket assay" in Methods and materials).

Figure 15:
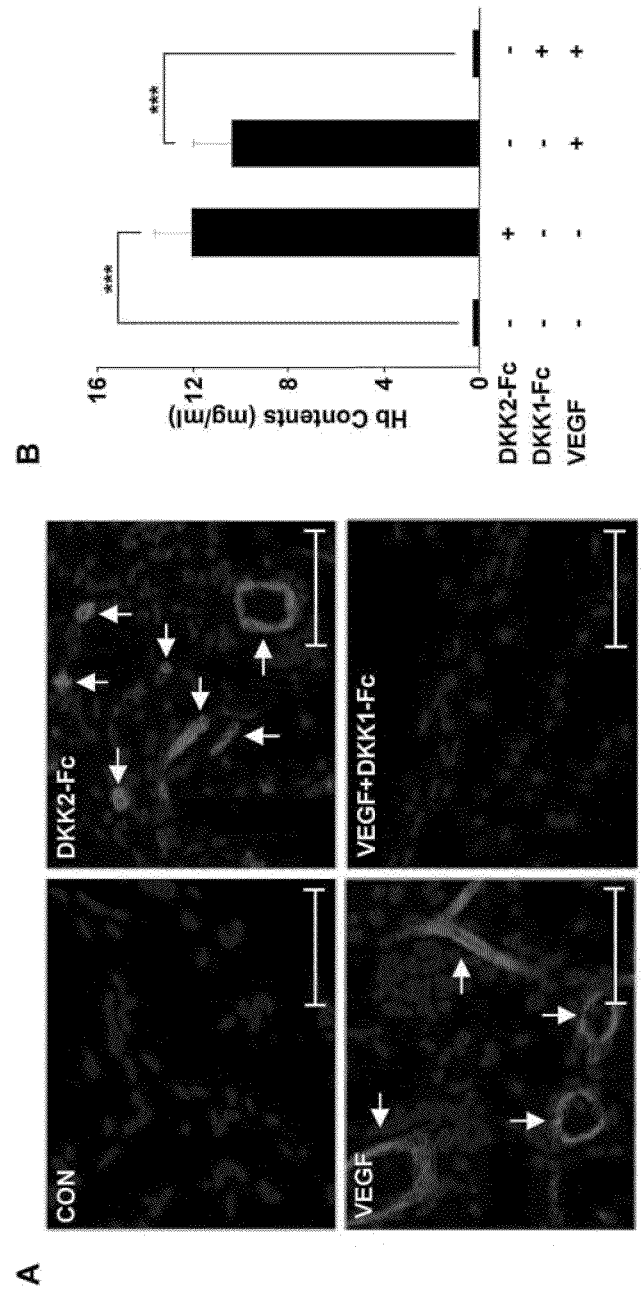
FIG. 15 is a group of views illustrating effects of DKK2 on angiogenesis, measured by in vivo Matrigel plug assay.

FIG. 15 is a group of views illustrating effects of DKK2 on angiogenesis, measured by In vivo Matrigel plug assay. In FIG. 15, Matrigel plug treated with VEGF (200 ng) and DKK2 (1 µg) were excised from mice 5 days after injection (n=5 per group). Scale bars: 100 µm. FIG. 15A is a group of photographs illustrating CD31 staining, and FIG. 15B is a graph illustrating a quantification of hemoglobin concentrations in a Matrigel plug. White arrows indicate CD31-stained vessels.

Figure 16:
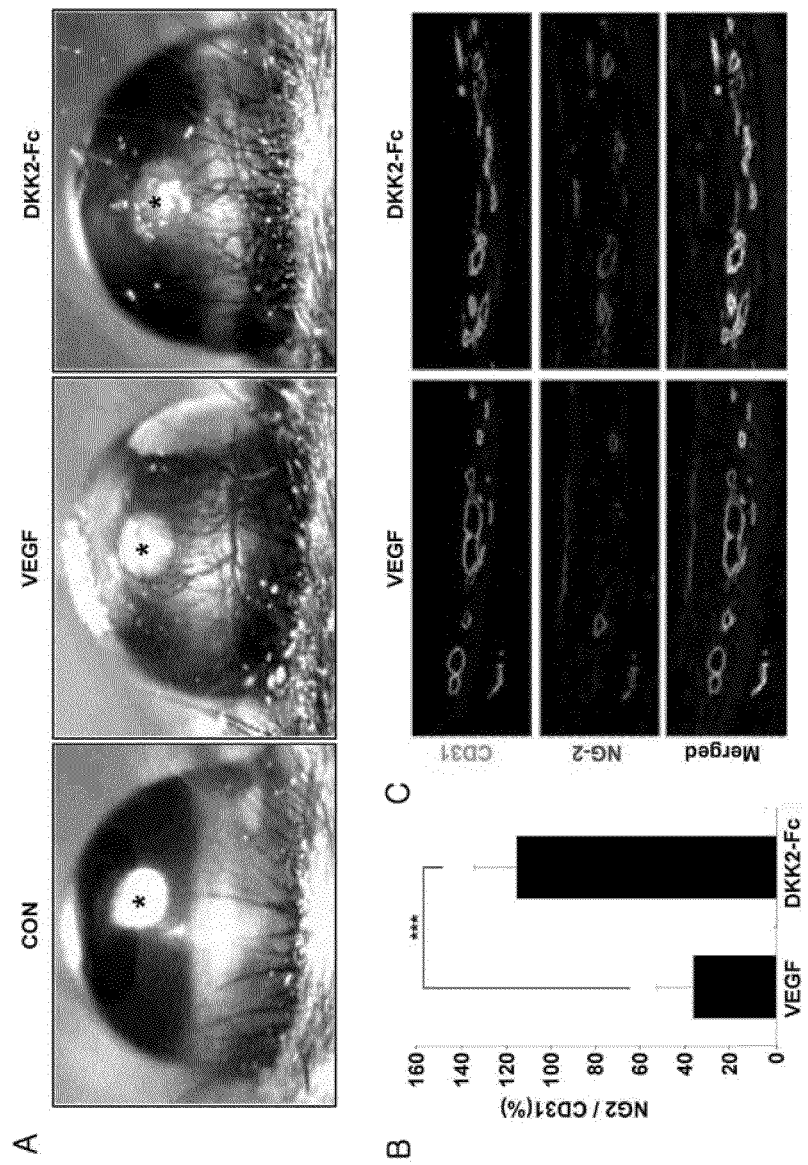
FIG. 16 is a group of views illustrating effects of DKK2 on angiogenesis, measured by mouse corneal pocket assay.

FIG. 16 is a group of views illustrating effects of DKK2 on angiogenesis, measured by mouse corneal pocket assay. FIG. 16A is a group of photographs illustrating results of corneal angiogenic responses induced by VEGF (200 ng)-, or DKK2-Fc (1 µg)-containing micropellets. An asterisk (*) indicates an inserted micropellet. FIG. 16C is a group of photographs illustrating results of CD31 and NG2 staining of cryosections of the eye. Green; CD31-positive, Red; NG2-positive, Blue; DAPI. FIG. 16B is a graph illustrating pericyte coverage calculated as a ratio of the NG2 to CD31 staining area (D).

Here, the ratio of the NG2 to CD31 represents a degree that vascular endothelial cells are covered. Data is the mean±S.D. (***p<0.001).

Figure 17:
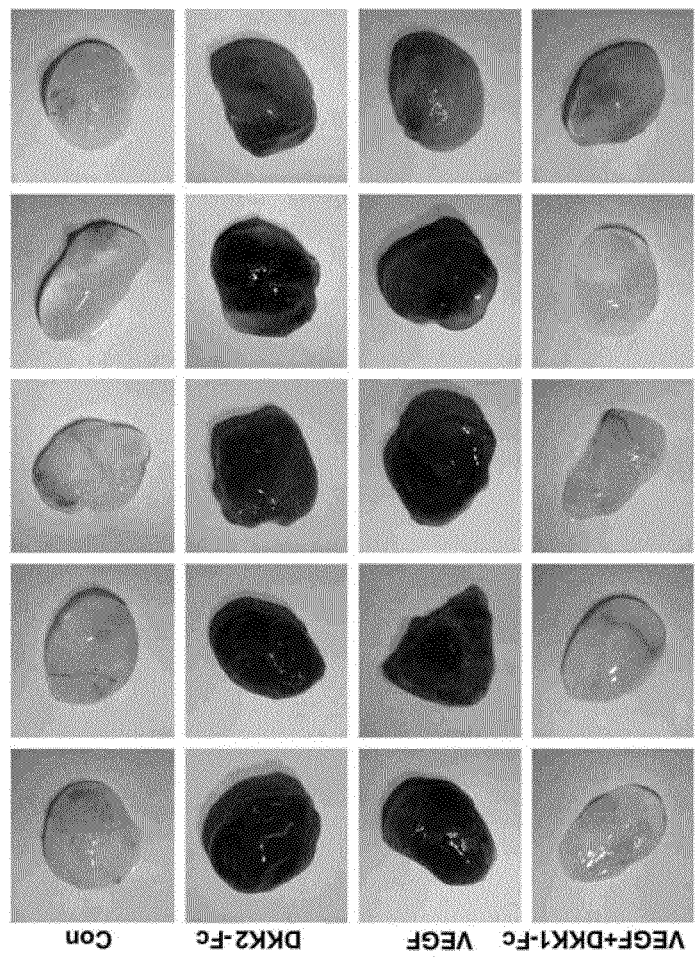
FIG. 17 is a group of photographs illustrating effects of recombinant DKK2 protein on vessel recruitment in Matrigel plugs.

FIG. 17 is a group of photographs illustrating effects of DKK2 recombinant protein on vessel recruitment in Matrigel plugs. C57BL/6 mice were injected with 0.6 ml of Matrigel containing VEGF (200 ng) and DKK2-Fc (1 μg) as indicated (n=5 per group). After 5 days, the mice were killed and Matrigel plugs were excised. FIG. 17 is a group of photographs of the excised plugs (n=5 per group).

As shown FIGS. 15-17, the color of Matrigel plugs treated with DKK2-Fc fusion or VEGF was red, indicating a neovascularization (FIG. 17, "VEGF" or "DKK2-Fc"). The color of Matrigel plugs co-treated with VEGF and DKK1-Fc fusion was similar to that of a control treated plug (FIG. 17, "VEGF+DKK1-Fc" and "Con"). Quantification of hemoglobin and CD31 staining of Matrigel Plugs consistently indicated that DKK2-Fc fusion significantly increases angiogenesis as compared to control-treated ones, while DKK1-Fc fusion suppresses VEGF-induced angiogenesis (FIGS. 15A and 15B).

The present inventors further examined the structural characteristics of DKK2-induced blood vessels in a mouse cornea pocket assay. As conventionally known, the growth of VEGF-induced blood vessels was relatively fast but their structure appeared to be disorganized and leaky (FIG. 16A). However, DKK2 induced well-organized vascular networks with distinct vascular tree-like structures (FIG. 16A). Consistently, DKK2-induced vessels showed more coverage of pericytes on ECs, which play an important role in vessel maturity and stability, as compared to VEGF-stimulated capillaries (FIGS. 16B and 16C).

EXAMPLE 4

Enhanced Angiogenic Sprouting and Filopodial Dynamics in DKK2 Tg Mice

Figure 18:
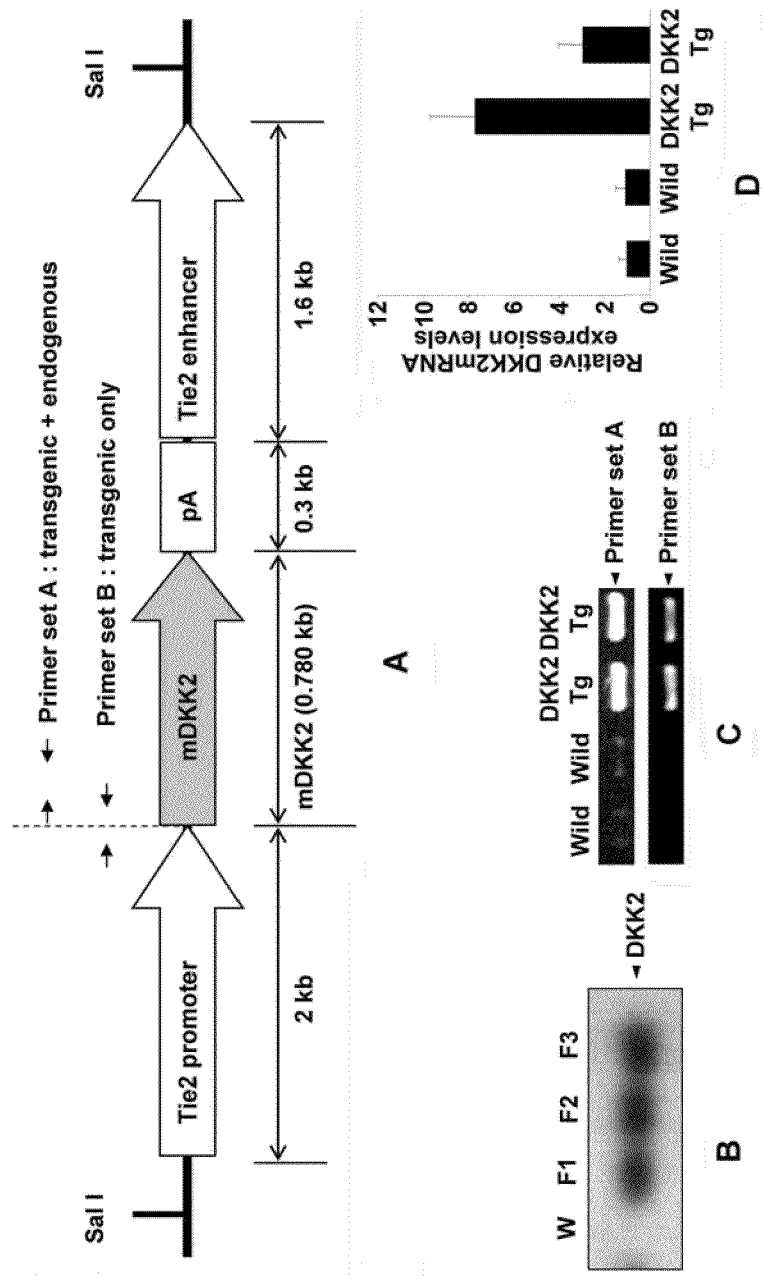
FIG. 18 is a group of views illustrating analysis results of gene constructs used to obtain EC-specific DKK2 transgenic (Tg) mice and the obtained EC-specific DKK2 Tg mice.

To further examine the angiogenic function of DKK2 in vivo, the present inventors generated transgenic (Tg) mice that express murine DKK2 (mDKK2) under the control of an EC-specific Tie2 promoter/enhancer (FIG. 18). The Tg mice were generated as described in Reference Example 3 as below.

FIG. 18 is a group of views illustrating analysis results of gene constructs used for generation of an EC-specific DKK2 Tg mice and EC-specific DKK2 Tg mice. FIG. 18A is a view illustrating a gene construct designed to allow DKK2 to be specifically expressed in endothelial cells. FIG. 18B is a photograph showing whether there are transgenes in founder mice, which may be confirmed with Western blotting. Three (DKK2) founder mice per group were identified. FIG. 18C is a photograph showing that total RNA was extracted from P12 mouse retinas, and Tg-specific DKK2 expression was confirmed with RT-PCR using primer set A (DKK2 cDNA-specific primer set: SEQ ID NOS: 5 and 6) and B (Tg-specific primer set: SEQ ID NOS: 7 and 8). FIG. 18D is a graph showing that RT-PCR using primer set A was performed.

In the three Tg mouse lines generated, the present inventors could not detect significant developmental abnormalities at the embryonic stage or in adults. However, in some cases, DKK2 Tg embryos showed slightly increased capillary density at E9.5 and higher age as compared to wild-type littermates.

Since retinal blood vessels are well characterized for their growth rate and patterning during early development, the present inventors analyzed DKK2 Tg phenotypes in the retina (See "(7) Analysis of mouse retinal vasculature" in Methods and materials).

Figure 19:
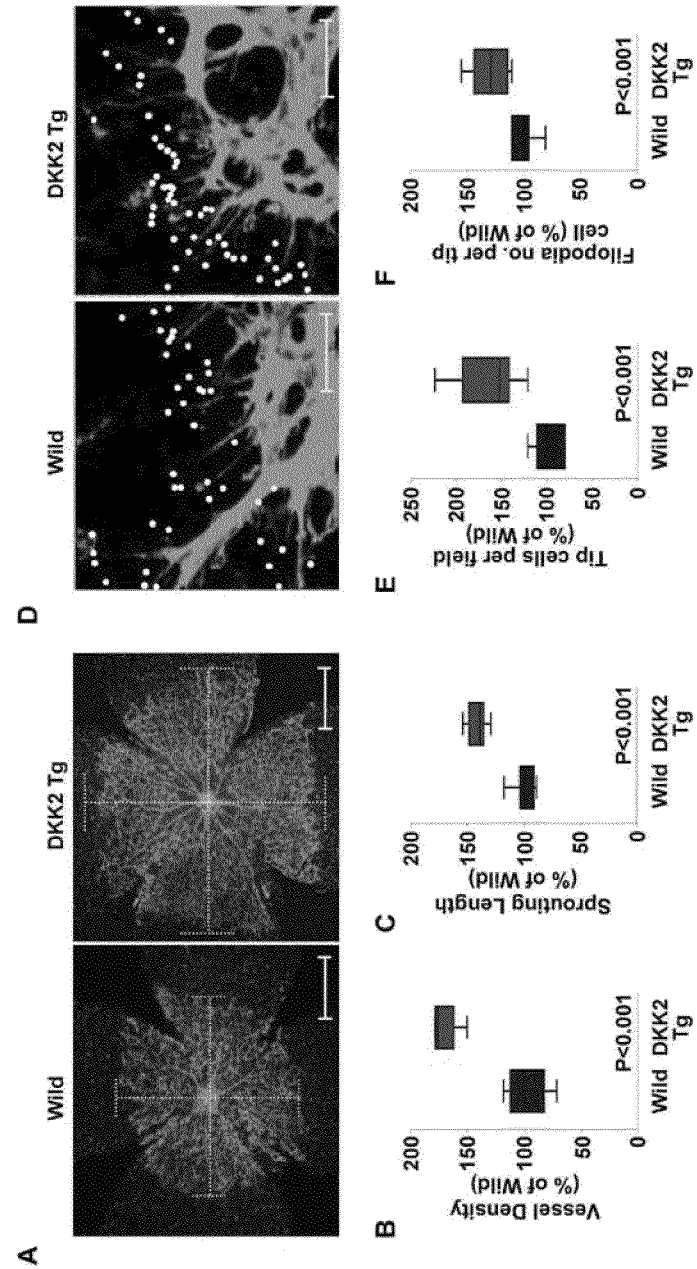
FIGS. 19 and 20 are views illustrating increases in retinal vessel formation in DKK2 Tg mice.
Figure 20:
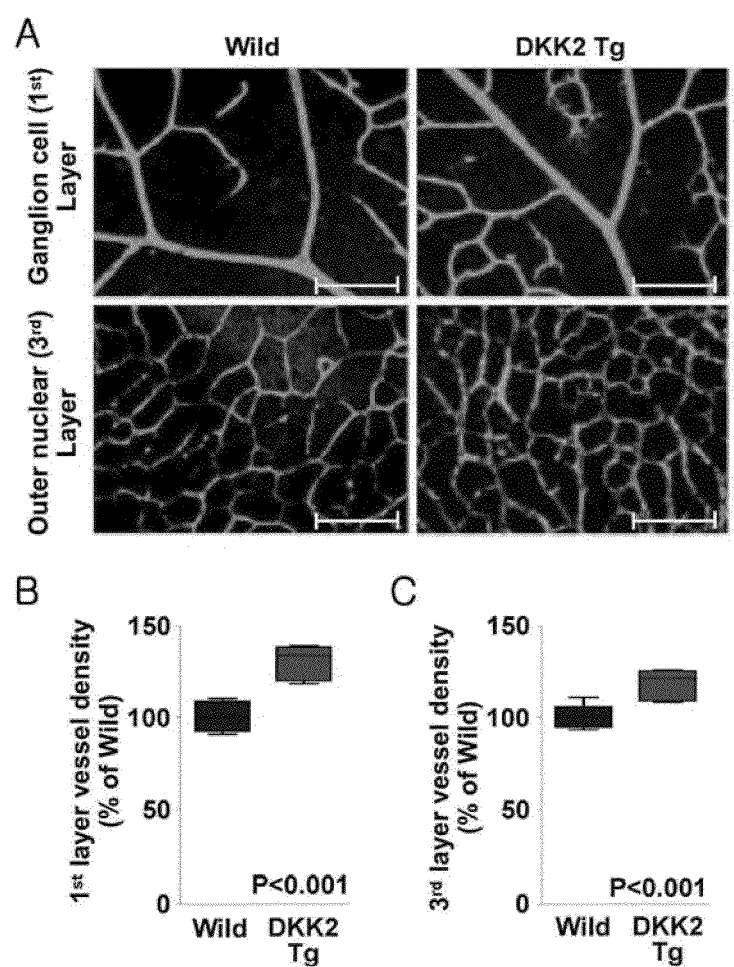

FIGS. 19 and 20 are views illustrating increases in retinal vessel formation in DKK2 Tg mice. FIGS. 19A and 19D are photographs illustrating isolectin B4 staining of whole-mounted P4 retinas of wild-type or DKK2 Tg mice. In FIG. 19A, white broken lines indicate the range of vessel extension. Scale bars: 100 μm. In FIG. 19D, white dots indicate filopodia extended from tip cells. FIG. 19B is a result of quantification of vessel densities, FIG. 19C shows sprouting length, FIG. 19E shows the number of tip cells, and FIG. 19F is the number of filopodia.

FIG. 20A is a group of photographs illustrating isolectin B4 staining of whole-mounted P12 retinas of wild-type or DKK2 Tg mice. Scale bars: 100 μm. FIG. 20B is a result of quantification of vessel density in a ganglion (1st) (H) and FIG. 20C is a vessel density in an outer nuclear (3rd) cell layer.

Figure 21:
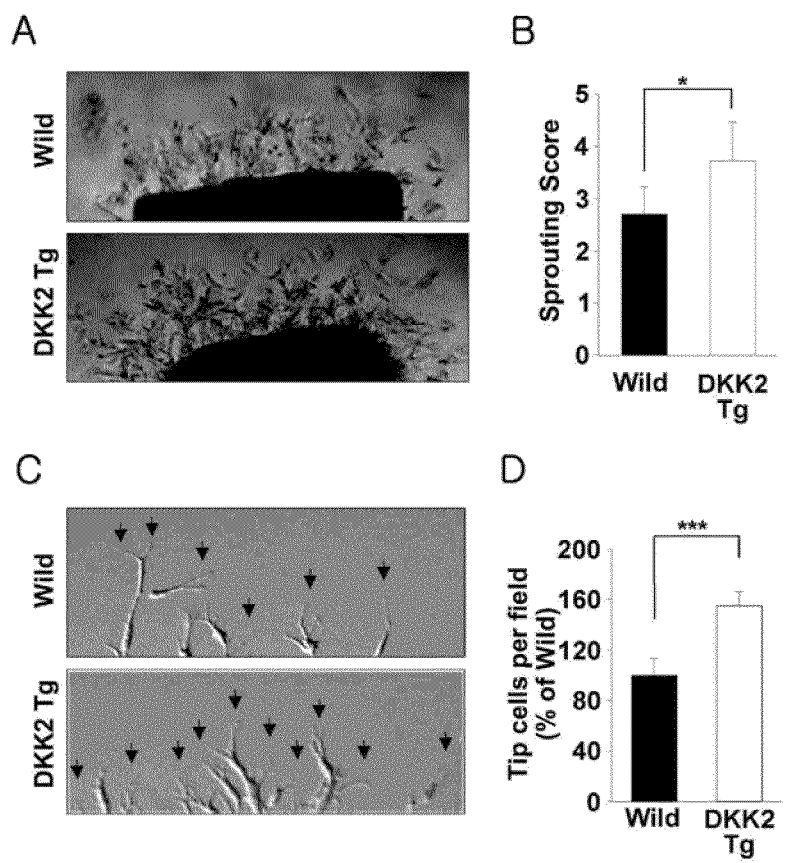
FIG. 21 is a group of views illustrating aortic segments harvested from wild-type and DKK2 Tg mice (n=7 per group)

FIG. 21 is a group of views illustrating aortic segments harvested from wild-type and DKK2 Tg mice (n=7 per group) (See "(6) Aortic ring assay" in Methods and materials). FIG. 21A is a group of photographs showing endothelial sprouts forming branching cords from the margins of aortic segments, which were photographed with a phase microscope. FIG. 21C is a group of photographs showing dynamic movement of endothelial sprouts from the margins of aortic segments, which was captured as real-time video. Arrows indicate filopodia. FIG. 21B shows sprouting scores and FIG. 21D is a result of quantification of tip cell numbers. Sprouting scores were scored from 0 (least positive) to 5 (most positive). Data is the mean±S.D. (*p<0.05, ***p<0.001).

Figure 22:
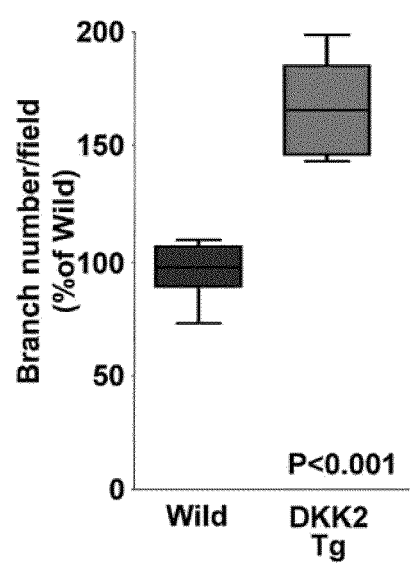
FIG. 22 shows results of quantification of vessel branching points in a ganglion layer (1st), measured by isolectin B4 staining of whole-mounted P12 retinas.

FIG. 22 shows results of quantification of vessel branching points in the ganglion layer (1st) as Isolectin B4 staining of whole-mounted P12 retinas.

Figure 23:
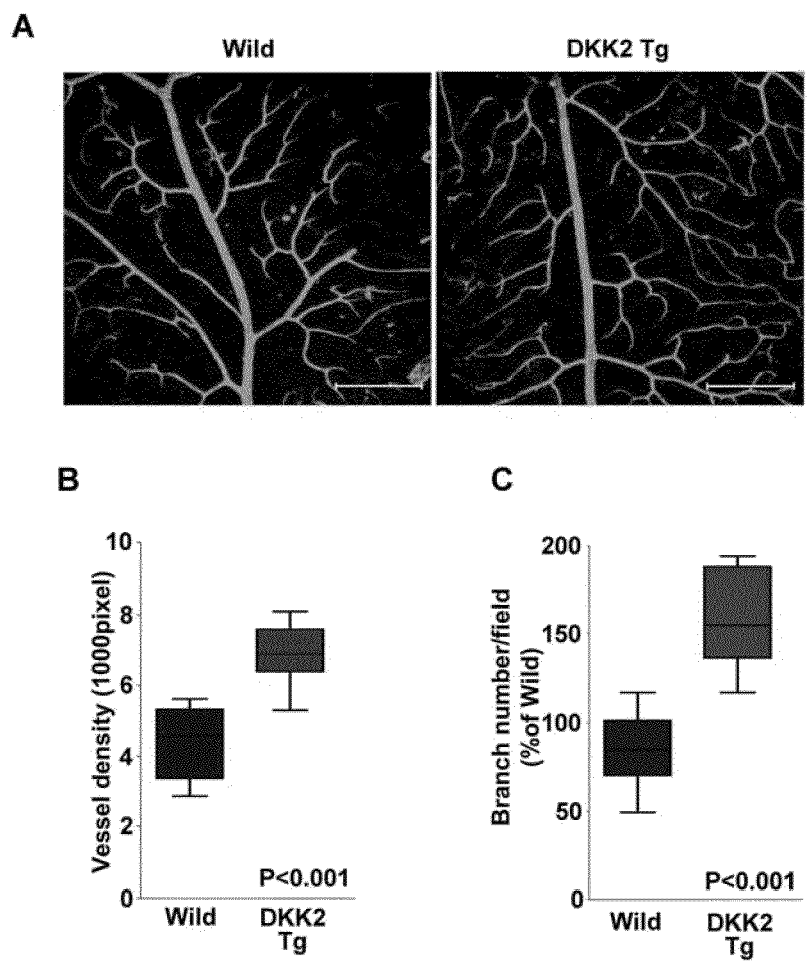
FIG. 23 shows images of retinas of 10 week old DKK2 Tg mice.

FIG. 23 is a group of views illustrating retinas of 10 week old DKK2 Tg mice. FIG. 23A is a group of photographs illustrating retina vessel staining of 10 week old wild (n=15) and DKK2 (n=9) Tg mice. Flat mounted retinas were analyzed by using confocal fluorescence microscopy (LSM 510 META). Scale bars: 200 μm. FIGS. 23B and 23C represent (B) relative vessel density and (C) branch number of Tg retina compared to wild-type. Density and branch number are measured by Multi Guage V2.2. Data is mean±SD (***p<0.001).

As described above, at P4, DKK2 Tg mice displayed increased vascular density and sprouting length in retinal vasculature compared to wild-type littermates (FIGS. 19A-C). Consistently, the numbers of tip cells and filopodia were also increased in DKK2 Tg mice (FIGS. 19D-F). In P12 retinas, the vascular density and branching of the ganglion layer (1st layer) as well as a sprouted plexus into a deeper layer (3rd layer) were markedly increased in DKK2 Tg mice (FIGS. 20A-C, and FIG. 22). Furthermore, an increase in retinal vascular density was maintained up to 10 weeks after birth (FIG. 23).

Consistently, in an ex vivo aortic ring assay, the average length and branch number of endothelial sprouts were increased in DKK2 Tg aortas compared to those from wild-type littermates (FIGS. 21A and 21B). In time-lapse video microscopy recorded over 9 hrs, DKK2 Tg aortas showed highly dynamic filopodial protrusion of tip cells (FIGS. 21C and 21D).

EXAMPLE 5

DKK2 Promotes New Vessel Formation in Both Hindlimb Ischemia and Myocardial Infarction Animal Models The present inventors next examined the effect of local injection of DKK2 protein on therapeutic neovascularization in a murine model of hindlimb ischemia. Hindlimb ischemia was induced by ligation and excision of the right femoral artery and vein, resulting in a severe vascular perfusion defect.

Figure 24:
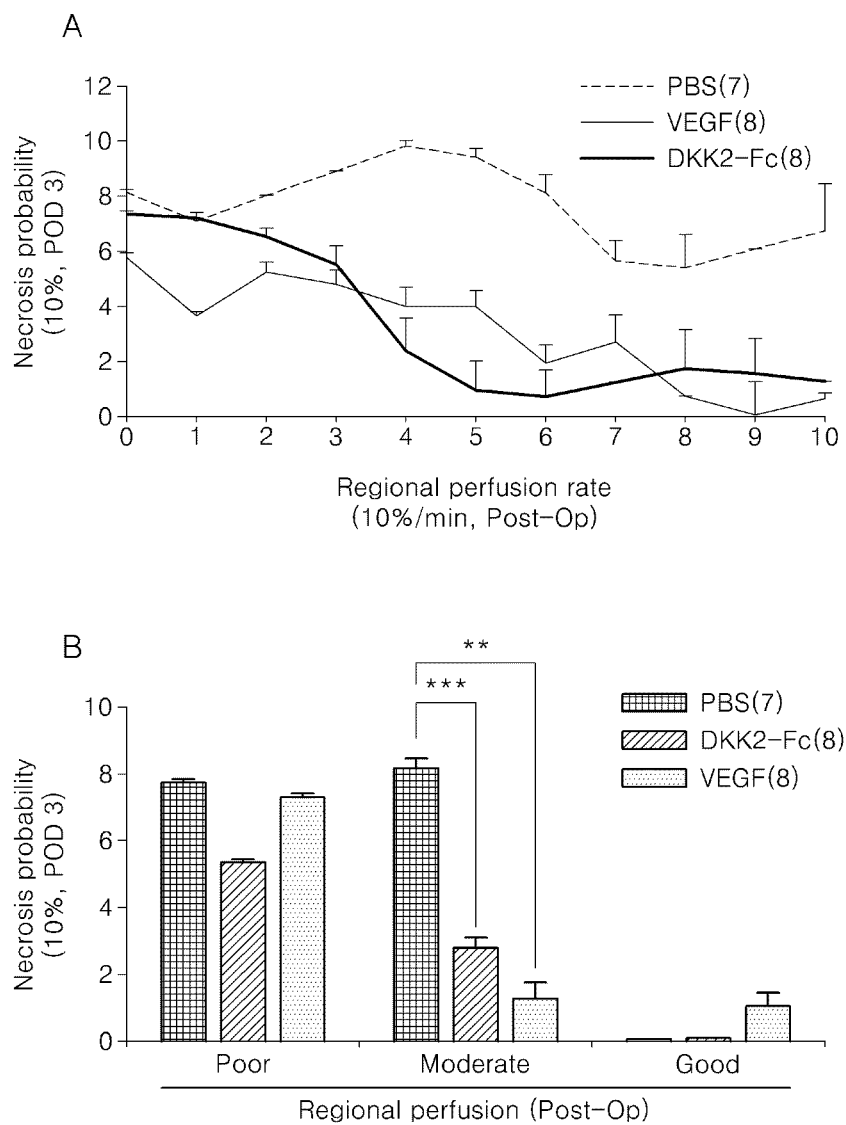
FIGS. 24-26 are views showing that DKK2 promotes angiogenesis to improve tissue recovery in animal models of both hindlimb ischemia and myocardial infarction.
Figure 25:
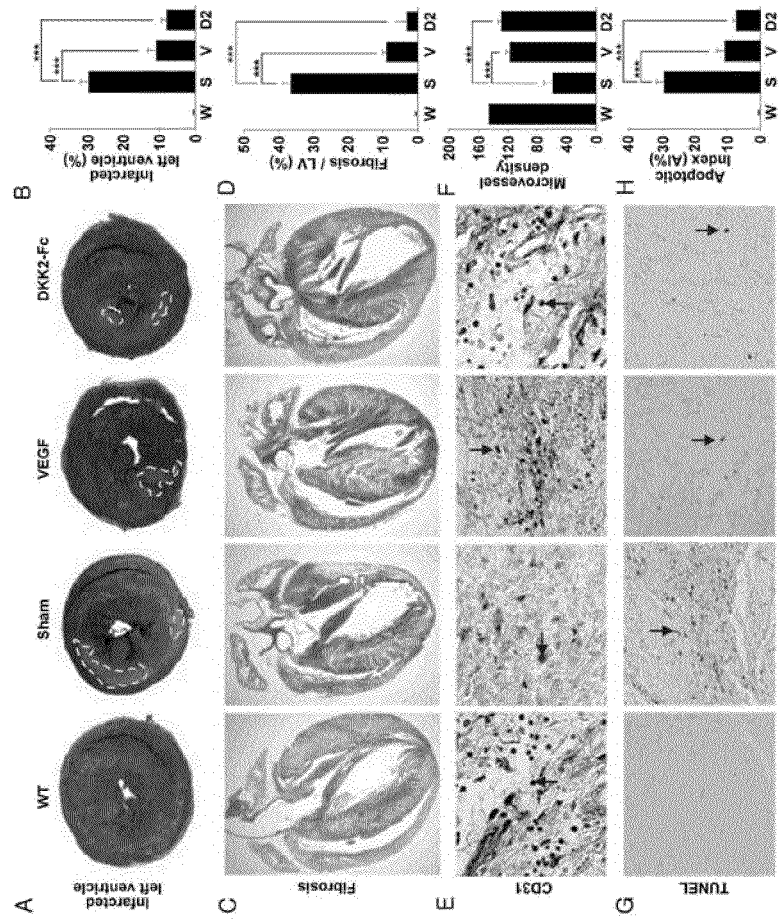
Figure 26:
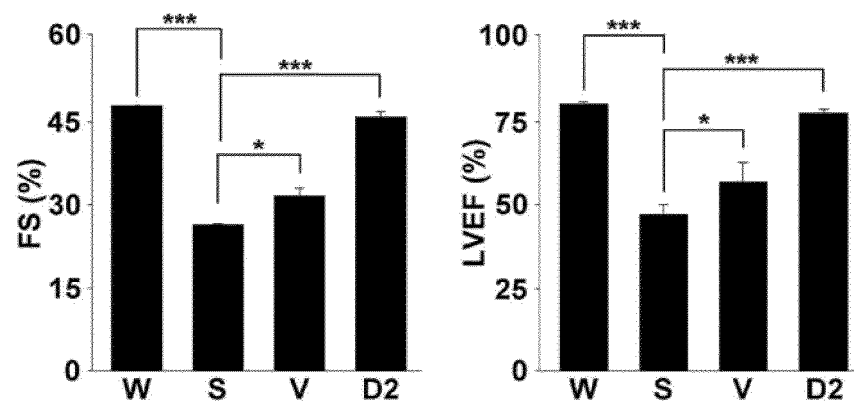

FIGS. 24-26 are views showing that DKK2 promotes angiogenesis to improve tissue recovery in animal models of both hindlimb ischemia and myocardial infarction. In the present Example, DKK2-Fc fusion (SEQ ID NO: 3) as a type of DKK2 was used.

FIG. 24 is a group of graphs illustrating effects of DKK2-Fc fusion on blood perfusion and the probability of necrosis in the ischemic hindlimb in mice. As shown in FIG. 24, intramuscular injection of DKK2-Fc fusion increased blood perfusion and reduced the probability of necrosis in the ischemic hindlimb in mice. FIG. 24 is a quantification of blood perfusion rate and necrosis probability (Poor perfusion rate: 0~30%/min, Moderate perfusion rate: 30~100%/min, Good perfusion rate: >100%/min).

FIG. 25 is a group of views showing that myocardial repair was increased after injection of DKK2-Fc fusion in a rat myocardial infarction model. FIGS. 25A and 25B are test results showing that myocardial injection of DKK2 greatly decreased an LV infarct size as assessed by TTC staining at 1 week post-MI. FIGS. 25C and 25D show representative images taken from a Masson's trichrome-stained section (muscle is stained red, and collagen is stained blue). FIGS. 25E and 25G show the microvessel staining with CD31 (E) and the TUNEL assay (G) on cardiac muscle tissues. FIGS. 25F and 25H show the quantitative analysis of microvessel density (F) and the TUNEL assay (H). A yellow broken lined area indicates the infarct region. Blue arrows indicate microvessels and apoptotic cells, respectively.

FIG. 26 is a group of graphs illustrating effective improvement of cardiac function by DKK2-Fc fusion injection. Cardiac functions were measured with two-dimensional conventional parameters: FS and LVEF measurements at 3 weeks after injection of DKK2 fusion into MI rats. FS(%)=[(LVEDD−LVESD)/LVEDD]×100(%). LVEDV=7.0×LVEDD3/(2.4+LVEDD), LVESV=7.0×LVESD3/(2.4+LVESD), and LVEF(%)=(LVEDV−LVESV)/LVEDV×100 (*p<0.05, p<0.01, *p<0.001). W; Wild-type, S; Sham, V; VEGF, and D2; DKK2-Fc fusion.

Figure 27:
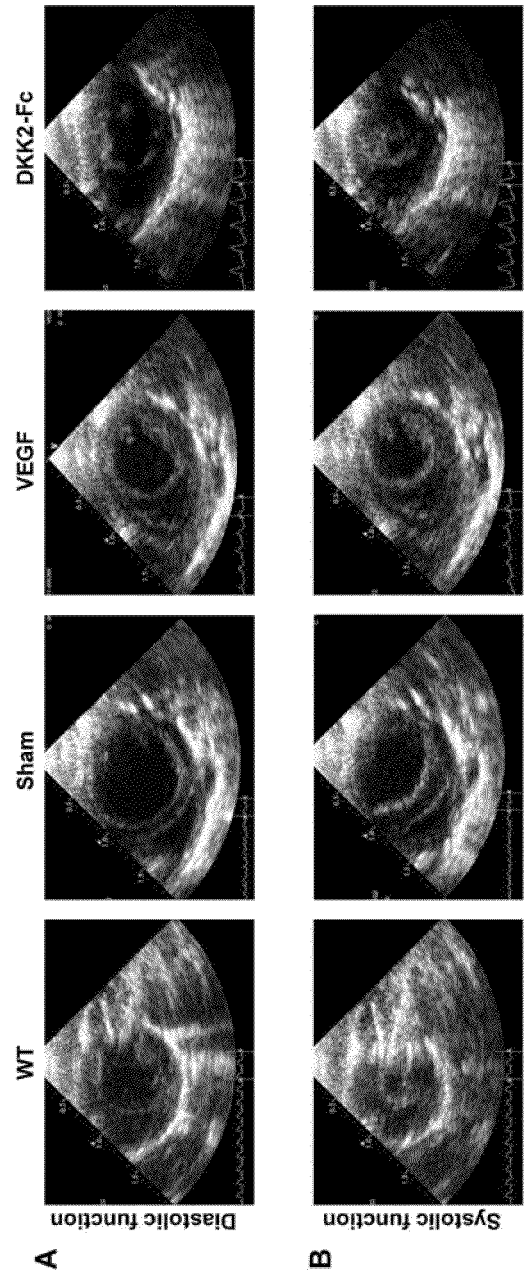
FIG. 27 shows images illustrating effective improvement of cardiac function following DKK2 injection.

FIG. 27 is a group of images illustrating effective improvement of cardiac function following DKK2 injection. The images represent diastolic function (A) and systolic function (B). Cardiac functions were measured with two-dimensional conventional parameters: fractional shortening (FS) and LV ejection fraction (EF) 3 weeks after injection of DKK2-Fc fusion into MI rats.

As a result, intramuscular injection of DKK2-Fc fusion resulted in a significant reduction in necrosis as compared to ischemic mice treated with phosphate-buffered saline (PBS) (FIGS. 24A and 24B). Indocyanine green (ICG) imaging revealed that blood perfusion was significantly improved at 3 days postsurgery in mice injected with DKK2-Fc compared to PBS-injected mice (FIGS. 24A and 24B), which is consistent with the hypothesis that the reduced necrosis was due to improved neovascularization in the ischemic limb.

The present inventors further assessed the therapeutic effect of DKK2-Fc fusion in a rat model of myocardial infarction (MI). One week after MI induction and DKK2-Fc fusion protein injection, the size of the left ventricular (LV) infarct was evaluated in the DKK2 and control (sham) groups. As a result, injection of DKK2-Fc fusion protein significantly decreased the infarct size and the degree of fibrosis in the infarct zone compared to the sham groups (FIGS. 25A-D). The mean microvessel count per field in the infracted heart was also higher (FIGS. 25E-F) and the incidence of TUNEL-positive myocardial cells was significantly reduced in the DKK2-Fc fusion group compared to the sham groups (FIGS. 25G and 25H).

Changes in cardiac function in DKK2 protein-treated MI animals were measured with transthoracic echocardiography. Echocardiography data (FIGS. 26 and 27 and Table 2) showed that DKK2-Fc fusion increased both LV fractional shortening (FS) and LV ejection fraction (EF) in the DKK2-Fc fusion group compared to the sham groups.

TABLE 2

|  | Wild-type (WT) | Control group (sham) | VEGF | DKK2-Fc fusion |
|---|---|---|---|---|
| LVEDD (mm) | 6.24 ± 0.41 | 7.87 ± 0.50 | 6.95 ± 0.38 | 6.38 ± 0.33 |
| LVESD (mm) | 3.15 ± 0.11 | 5.88 ± 0.42 | 4.83 ± 0.49 | 3.39 ± 0.23 |
| FS (%) | 49.15 ± 1.83 | 25.31 ± 0.56 | 30.62 ± 3.20 | 46.89 ± 0.84 |
| LVEF (%) | 79.61 ± 1.55 | 48.31 ± 1.15 | 56.68 ± 4.96 | 77.28 ± 1.06 |

Table 2 shows effective improvement of cardiac function by DKK2-Fc fusion injection. Injection of DKK2-Fc fusion or VEGF showed further improvement in systolic performance and cardiac dimensions compared to sham group animals. However, cardiac dimensions including LV end diastolic diameter (LVEDD) and LV end systolic diameter (LVESD) were smaller in the DKK2-Fc fusion treated group compared to the VEGF treated group (FIG. 27 and Table 2).

The DKK2-Fc fusion treated group experienced a further increase in systolic performance (16.27% increment in % FS and 20.5% increment in % EF) compared to the VEGF group (FIGS. 26 and 27, and Table 2).

EXAMPLE 6

DKK2 Induced Filopodial Extrusion of ECs Requires Cdc42 Activation

The present inventors next scrutinized the mechanism of action of DKK2 in the vasculature. Previous studies show that tip cell filopodial extension in the developing retina depends on astrocyte-derived VEGF-A acting directly on tip cells. However, glial fibrillary acidic protein (GFAP) and VEGF-A mRNA levels, as well as relative levels of VEGF-A splice isoforms, remained unchanged in DKK2 Tg mice compared to wild-type mice (FIG. 28), suggesting that DKK2 may directly act to the tip cells of ECs.

Figure 28:
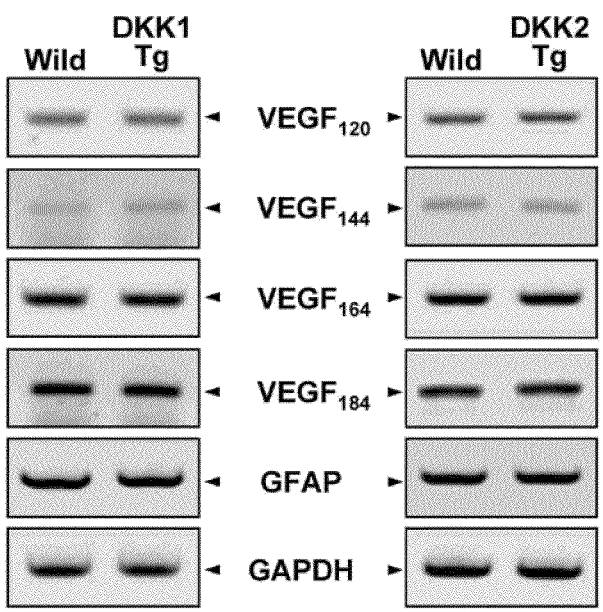
FIG. 28 is a group of photographs illustrating effects of DKK1 and DKK2 on expression of VEGF isoforms and GFAP.

FIG. 28 is a group of photographs illustrating effects of DKK1 and DKK2 on expression of VEGF isoforms and GFAP. RT-PCR analysis detects VEGF isoforms and GFAP in the retina at P4.

Tips of sprouts are composed of highly migratory cells with numerous filopodia and lamellipodia-like processes, which are conferred by the action of small GTPases, such as Cdc42. Therefore, the present inventors hypothesized that DKK2 may stimulate tip cell filopodial extension through regulating the activation of Cdc42.

Figure 29:
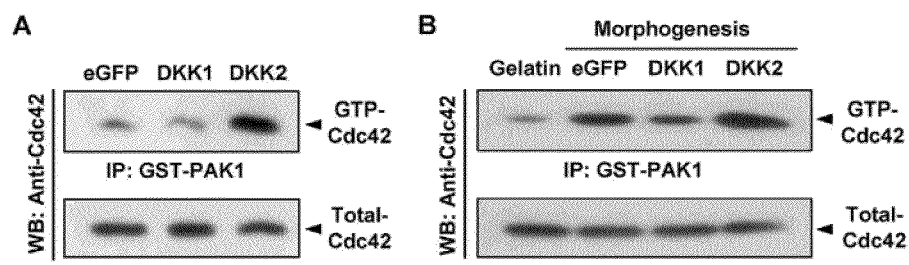
FIG. 29 is views showing that DKK2 increases filopodial protrusions in a Cdc42 dependent manner.

FIG. 29 is a view showing that DKK2 increases filopodial protrusions in a Cdc42 dependent manner. FIG. 29A shows that HUVECs stably expressing eGFP, DKK1, or DKK2 were analyzed for Cdc42 activities. The introduction of eGFP, DKK1, or DKK2 genes was performed via a lentiviral vector, as described in FIG. 3. FIG. 29B shows that stable transfectants were cultured on a Matrigel-coated plate (morphogenesis) for 2 hrs and Cdc42 activities were measured. Cdc42 activity was measured with a CDC42 activation kit, which is commercially available, according to the manufacturer's instructions. The kit is a kit for measuring GTP-Cdc42 and the total amount of Cdc42 was identified by Western blotting.

Figure 30:
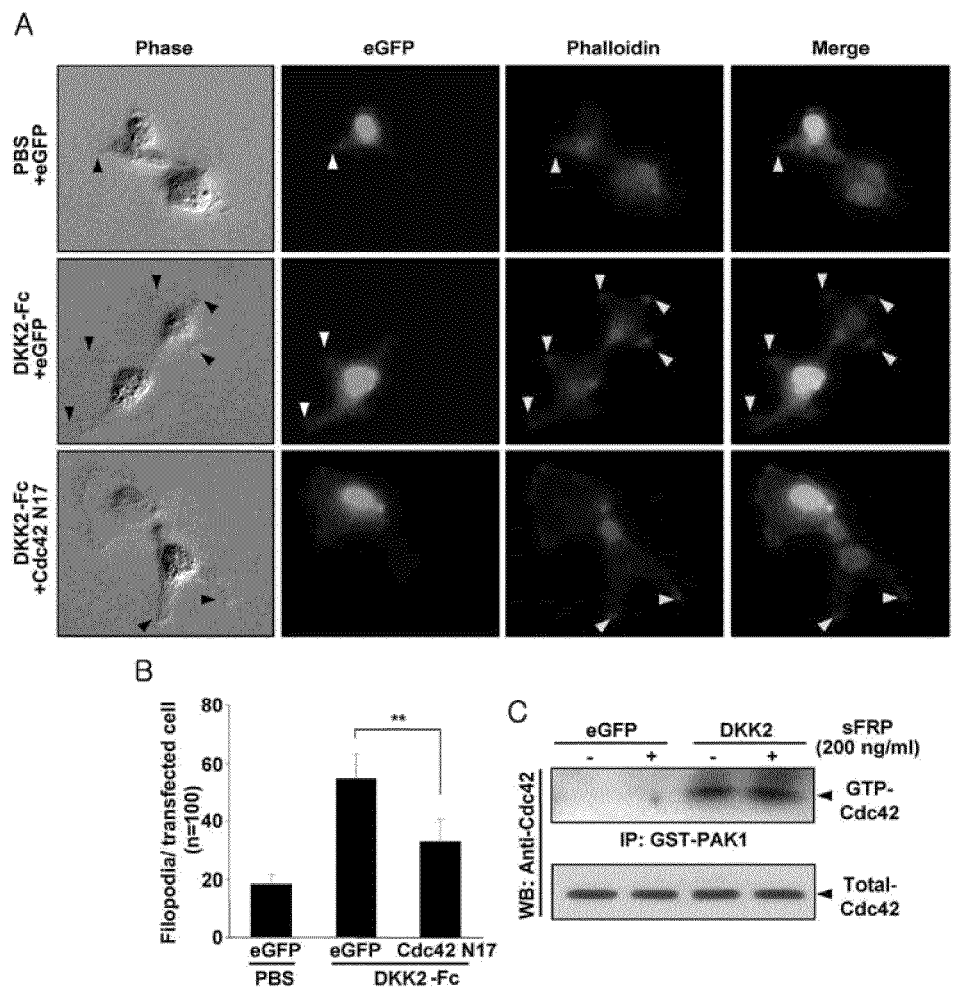
FIG. 30 is a group of views illustrating effects of DKK2 on filopodial extension in HUVECs and that DKK2 increases filopodial protrusions in a Cdc42 dependent manner.

FIG. 30 is a group of views illustrating effects of DKK2 on filopodial extension in HUVECs. FIG. 30 is also views showing that DKK2 increases filopodial protrusions in a Cdc42 dependent manner (FIG. 30C). In FIGS. 30A and 30B, HUVECs were transiently transfected with expression plasmids encoding eGFP control or eGFP plus Cdc42 (N17). For eGFP, a pGL3 vector was used as described in FIG. 2, whereas for Cdc42 (N17), a lentiviral vector was used as described in FIG. 3. Herein, eGFP-Cdc42 (N17) indicates that eGFP is fused to the N-terminal of Cdc42 (N17), a dominant negative mutant of human Cdc42. Cdc42 (N17) has threonine (T), the $17^{th}$ amino acid of human Cdc42, substituted for asparagine (N) and inhibits the normal activation of Cdc42. After 24 hrs, these cells were plated on Matrigel-coated plates and incubated with PBS or DKK2-Fc fusion (1.5 µg/ml) for 2 hrs. Then, microphotographs were taken (A) and filopodia number was quantified (B). Arrowheads indicate filopodial extension. Data is mean±SD (**p<0.01). FIG. 30C shows that HUVECs stably expressing eGFP or DKK2 were incubated with sFRP (200 ng/ml) for 24 hrs and Cdc42 activity was measured.

Figure 31:
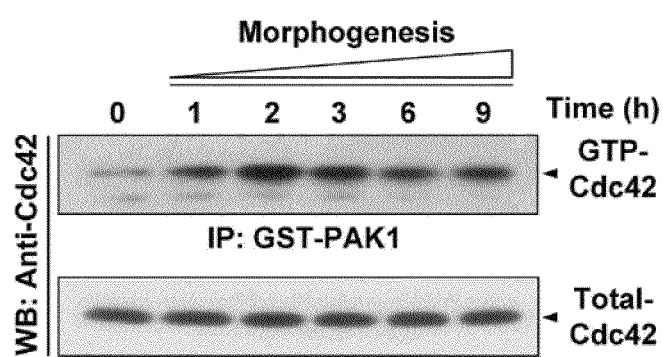
FIG. 31 shows photographs illustrating a change in expression of Cdc42 during morphogenesis.

FIG. 31 is a group of photographs illustrating a change in expression of Cdc42 during morphogenesis. In FIG. 31, HUVECs were plated on Matrigel-coated plates (morphogenesis) and cultured for the indicated times. Next, Cdc42 activity was measured.

Figure 32:
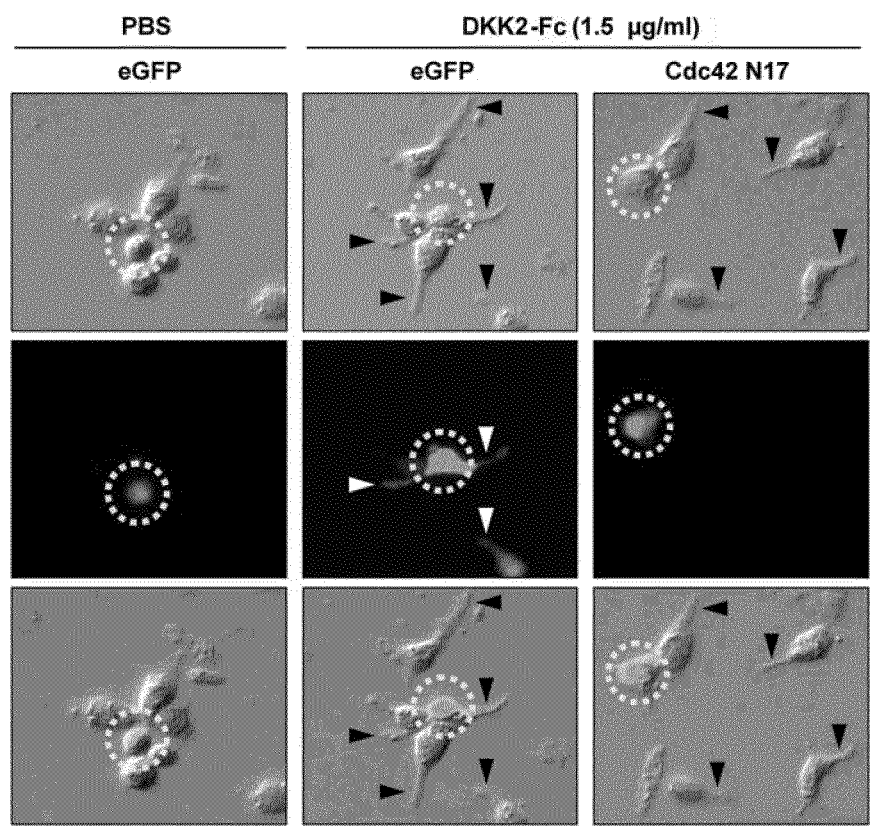
FIG. 32 shows photographs illustrating effects of DKK2 on filopodial extension.

FIG. 32 is a group of photographs illustrating effects of DKK2 on filopodial extension. In FIG. 32, HUVECs were transiently transfected with expression plasmids encoding the eGFP control group or eGFP plus dominant negative mutants of Cdc42 (Cdc42 (N17)). For eGFP, a pGL3 vector was used as described in FIG. 2, whereas for Cdc42 (N17), a lentiviral vector was used as described in FIG. 3. Transfection by the pGL3 vector was performed by incubating lipofectamin and expression vectors and then adding them to cells in a medium. After 24 hrs, cells were plated on Matrigel-coated plates and incubated with PBS or DKK2-Fc fusion protein (1.5 µg/ml) for 2 hrs. Then, microphotographs were taken. White and black arrowheads indicate filopodial extension. Yellow broken circles indicate transfected cell.

In HUVECs cultured on gelatin, overexpression of DKK2 induced Cdc42 activation to increase the amount of GTP-Cdc42, whereas DKK1 did not induce Cdc42 activation (FIG. 29A). During EC morphogenesis, Cdc42 was spontaneously activated in EC plated on Matrigel and its activation was slightly potentiated in the DKK2-expressing ECs, but significantly reduced in the DKK1-expressing cells (FIGS. 29B and 31). Also, filopodial protrusion was significantly increased by the treatment of DKK2-Fc fusion protein at 2 hr compared to the control and a dominant negative form of Cdc42 blocked DKK2-Fc fusion protein-induced filopodial extensions (FIGS. 30A and 30B, and FIG. 32). These results suggest that DKK2 may promote angiogenesis at least in part by endowing the dynamics of tip cell structures, which require Cdc42 activation and filopodial protrusion.

To identify the supporting mechanism of DKK2-mediated Cdc42 activation in ECs, the present inventors determined whether the WNT/Frizzled complex or LRP5/6 is involved in the signaling events induced by DKK2. Treatment of soluble Frizzled related protein (sFRP)(R&D Systems: sFRP-1), a decoy antagonist of WNT, did not inhibit DKK2-mediated Cdc42 activation (FIG. 30C).

FIGS. 33-37 are views showing that DKK2-induced Cdc42 activation requires LRP6-mediated Adenomatous Polyposis Coli (APC)/Asef2 signaling.

Figure 33:
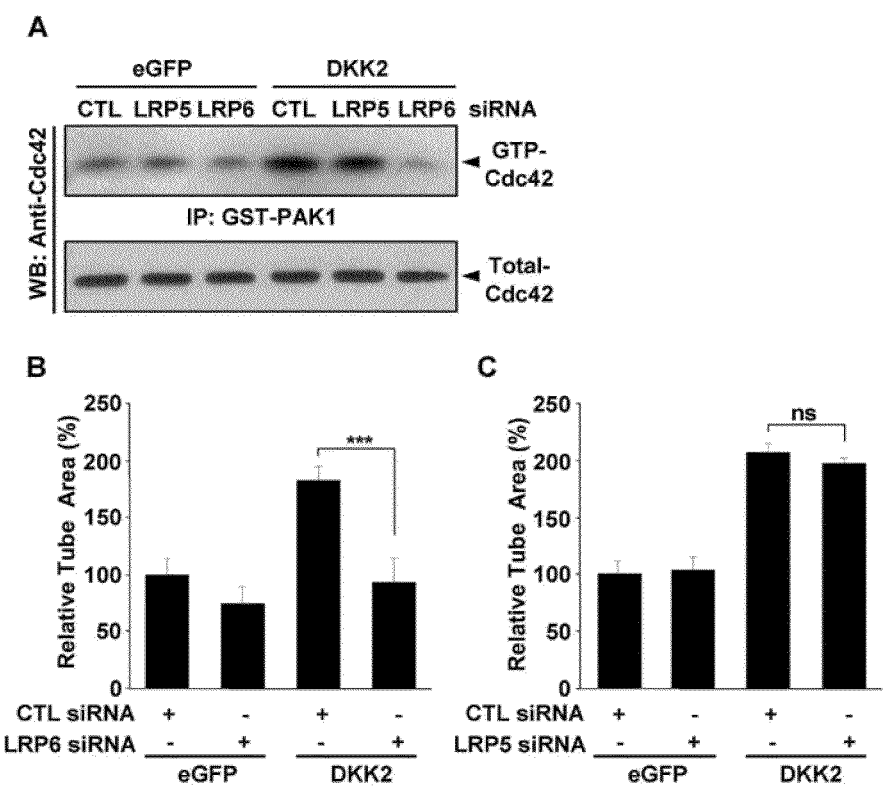
FIGS. 33-37 are views showing that DKK2-induced Cdc42 activation requires LRP6-mediated Adenomatous Polyposis Coli (APC)/Asef2 signaling.

FIG. 33 is a group of views showing that HUVECs stably expressing eGFP or DKK2 were transfected with control siRNA (CTL), LRP5- or LRP6-specific siRNA. Herein, the control siRNA employed a sequence which is not complementary to a transcriptome of LRP5-, LRP6- or other genes as a random sequence, and the LRP5-specific siRNA and LRP6-specific siRNA have sequences which are complementary to LRP5 and LRP6, respectively. HUVECs stably expressing eGFP or DKK2 were manufactured in the same manner as described in FIG. 4, and transfection of siRNA was performed by incubating the siRNA with lipofectamin and then adding the mixture to cells in a medium.

FIG. 33A shows Cdc42 activity after 60 hrs, which was measured by Western blotting. Cells were plated on Matrigel-coated plates at a density of $1.5 \times 10^5$ cells/well and incubated for 18 hrs. FIGS. 33B and 33C show a result that microphotographs were taken of HUVECs transfected with LRP6-specific siRNA (B) or LRP5-specific siRNA (C), and capillary-like networks were quantified with Image-Pro Plus software. Data is mean±SD (***p<0.001, ns; not significant).

Figure 34:
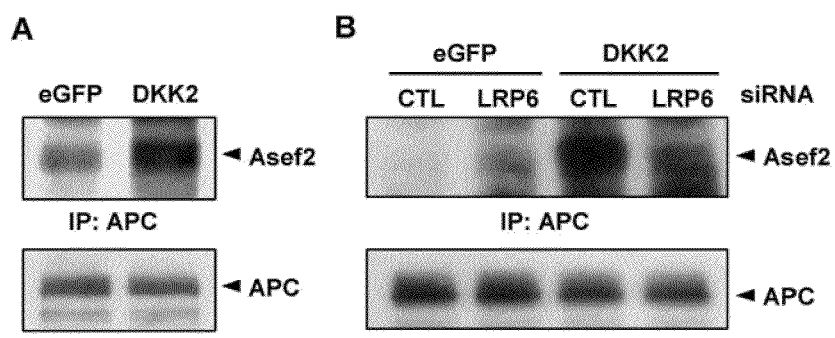

FIG. 34 is a group of photographs illustrating expression of APC/Asef2 in HUVECs stably expressing DKK2. HUVECs stably expressing DKK2 were prepared in the same manner as described in FIG. 4. FIG. 34A shows co-immunoprecipitation of APC with Asef2 for HUVECs stably expressing DKK2. Lysates were prepared from cells overexpressing eGFP or DKK2, immunoprecipitated with anti-APC antibody, and probed with anti-Asef2 or anti-APC antibodies. FIG. 34B shows that eGFP or DKK2 expressing cells were transiently transfected with control siRNA or LRP6-specific siRNA. After 60 hrs of cell incubation, cell lysates were subjected to co-immunoprecipitation. Here, the control siRNA (F—H) employed a sequence which is not complementary to a transcriptome of LRP6- or other genes as a random sequence, and the LRP6-specific siRNA has a sequence which is complementary to mRNA of LRP6 gene. Also, transfection of siRNA was performed by being incubated with lipofectamin for 30 mins and then adding the mixture to cells in a medium.

Figure 35:
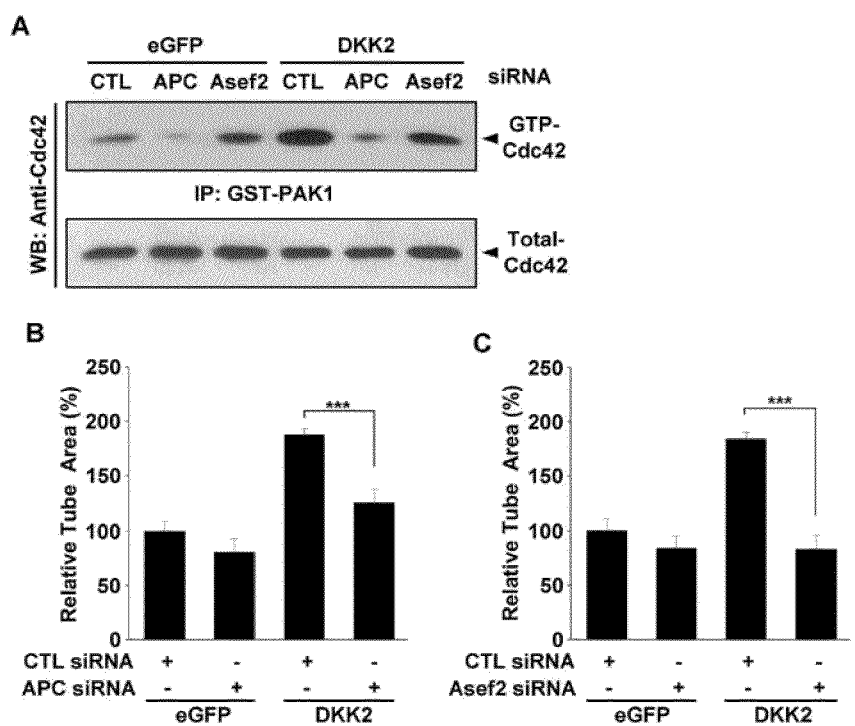

FIG. 35 shows a result that eGFP or DKK2 expressing cells were transiently transfected with control siRNA, APC- or Asef2-specific siRNA. HUVECs stably expressing eGFP or DKK2 were prepared in the same manner as described in FIG. 4, and the transfection of siRNA was performed by being incubated with lipofectamin for 30 mins and then adding the mixture to cells in a medium. Here, the control siRNA employed a sequence which is not complementary to a transcriptome of APC-, Asef2- or other genes as a random sequence, and the APC-specific siRNA and Asef2-specific siRNA have a sequence which is complementary to an APC gene and an Asef2 gene, respectively. FIG. 35A shows a result that transfected HUVEC cells were incubated for 60 hrs and then Cdc42 activity was measured by Western blotting. FIGS. 35B and 35C show a result of cells transiently transfected with APC-specific siRNA (B) or Asef2-specific siRNA (C) being plated on Matrigel-coated plates at a density of $1.5 \times 10^5$ cells/well and incubated for 18 hrs. Capillary-like networks were measured with Image-Pro Plus software.

Figure 36:
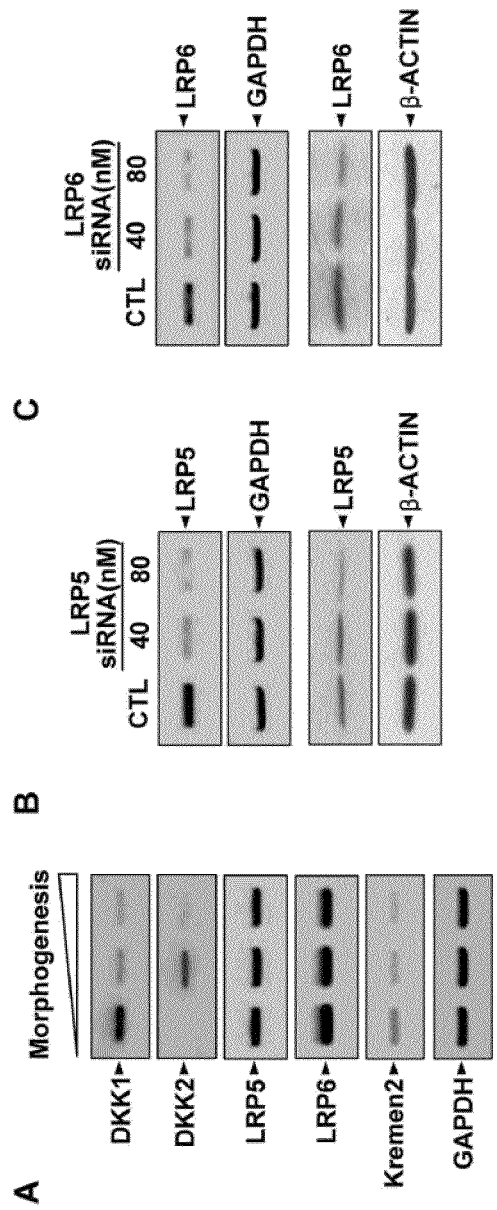
Figure 37:
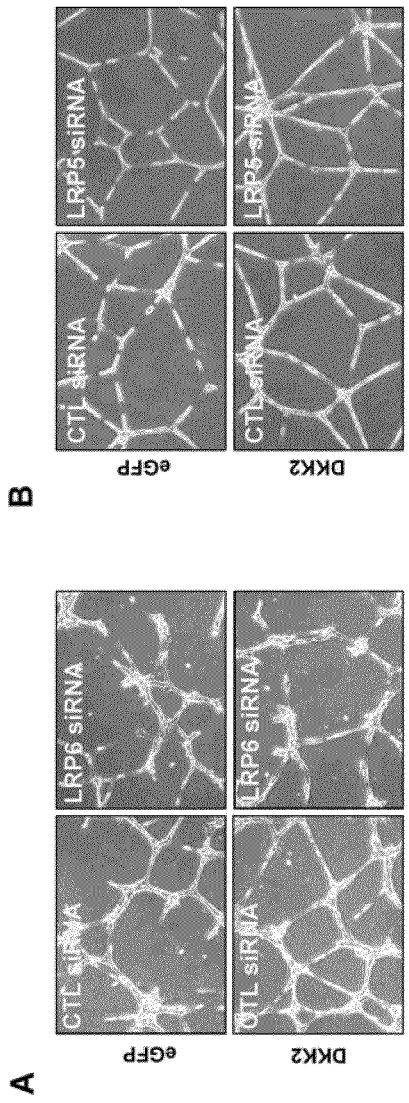

FIGS. 36 and 37 are photographs showing that the DKK2 receptor in HUVECs is LRP6. In FIG. 36A, mRNA levels of DKK1, DKK2, LRP5, and LRP6 were measured by RT-PCR at 0.5, 8, and 18 hrs during morphogenesis of ECs. In FIGS. 36B and 36C, HUVECs were transiently transfected with control siRNA (CTL), LRP5-specific siRNA (B), or LRP6-specific siRNA (C). The transfection was performed by incubating the siRNA with lipfectamin for 30 mins and then adding the mixture to cells in a medium. After 40 hrs (for mRNA) or 60 hrs (for protein), mRNA and protein levels were measured by RT-PCR (upper portion) and Western blotting (lower portion). In FIG. 37, HUVECs stably expressing eGFP or DKK2 were transiently transfected with LRP5 specific siRNA (B) or LRP6 specific siRNA (A). The transfection was performed by incubating the siRNA with lipofectamin for 30 mins and then adding the mixture to cells in a medium. Cells were plated on Matrigel-coated plates at a density of $1.5 \times 10^5$ cells/well and incubated for 18 hrs. Microphotographs were taken.

Figure 38:
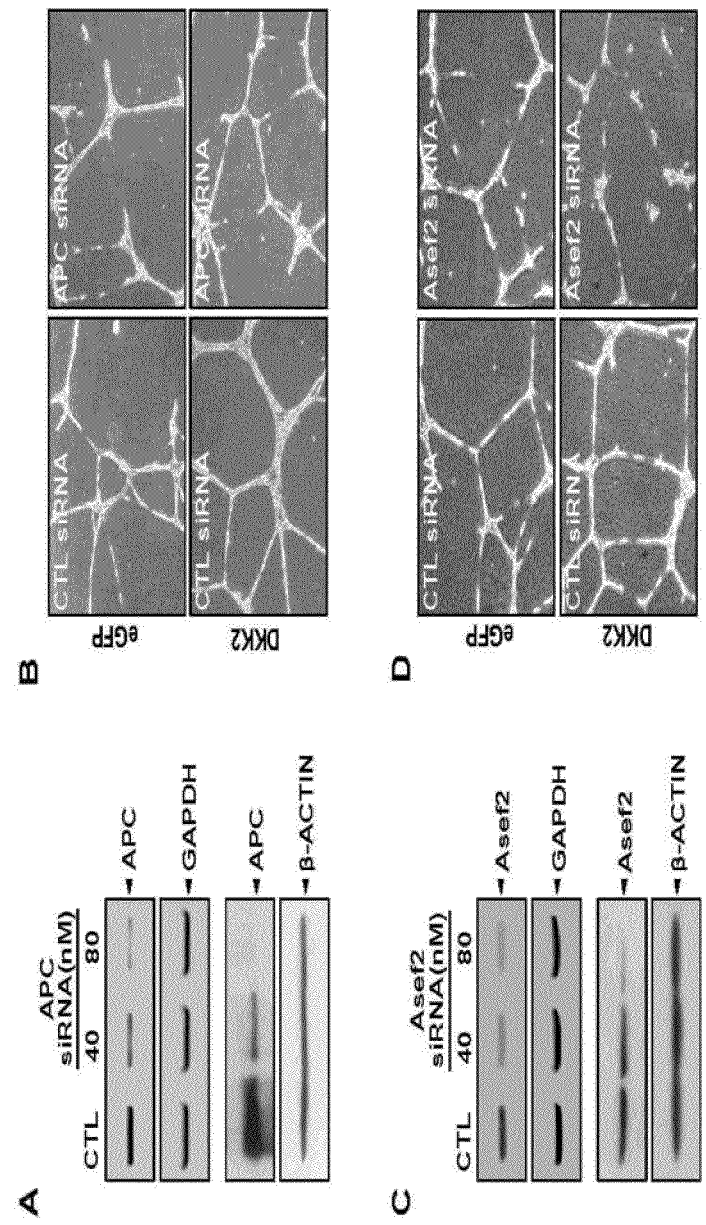
FIG. 38 is a group of photographs illustrating effects of APC and Asef2 on DKK2-induced EC morphogenesis.

FIG. 38 is a group of photographs illustrating effects of APC and Asef2 on DKK2-induced EC morphogenesis. In FIGS. 38A and 38C, HUVECs were transiently transfected with siRNA (CTL), APC-specific siRNA or Asef2-specific siRNA. After 60 hrs (for mRNA) or 80 hrs (for protein) of incubation, mRNA and protein levels were measured by RT-PCR (upper portion) and Western blotting (lower portion). FIGS. 38B and 38D show a result of HUVECs stably expressing eGFP or DKK2 being transiently transfected with control siRNA (CTL), APC-specific siRNA or Asef2-specific siRNA. After 60 hrs of incubation, cells were plated on Matrigel-coated plates at a density of $1.5 \times 10^5$ cells/well and incubated for 18 hrs, and microphotographs were taken.

Interestingly, knock-down experiments of LRP5 and LRP6 revealed that LRP6, but not LRP5, was importantly involved in DKK2-mediated Cdc42 activation, although both LRPs are expressed in ECs (FIG. 33A and FIGS. 36A-C). Consistently, siRNA specific to LRP6 completely blocked DKK2-induced EC morphogenesis, whereas siRNA against LRP5 had no significant effect (FIGS. 33B and 33C, and FIGS. 37A and 37B). These results suggest that DKK2 activates the Cdc42 signaling pathway via LRP6 and independent of WNT/Frizzled signaling.

It has recently been reported that APC protein stimulates the GEF activity of APC-stimulated-exchange-factor (Asef)$_2$, a guanine-nucleotide exchange factor (GEF) specific for Cdc42.

Since APC is one of the components working downstream of LRP6, the present inventors hypothesized that DKK2 stimulation of LRP6 might induce APC/Asef2 complex formation, resulting in Cdc42 activation. Indeed, APC and Asef2 interaction was prominently increased in ECs expressing DKK2 and was blocked by LRP6 siRNA (FIGS. 34A and 34B). Moreover, knock-down of APC or Asef2 inhibited the Cdc42 activation and EC morphogenesis induced by DKK2 (FIGS. 35A-C and FIG. 38). Taken together, these results suggest that the angiogenic action of DKK2 might be mediated through its cognate receptor LRP6 in ECs and APC/Asef2 complex at least lies downstream of LRP6 that leads to Cdc42 activation and stimulation of tip cell dynamics.

REFERENCE EXAMPLE 1

Cultivation of HUVEC

HUVECs (Human umbilical vein endothelial cell) were isolated from the umbilical cords obtained from gynecology department of Yonsei University Hospital according to following process. After washing veins with Cord buffer (0.2% glucose phosphate buffered saline), 5 ml of 0.2% type I collagenase (Sigma-Aldrich Co., MO, USA) was added to the veins and the veins were left alone at 37° C. for 5 min. After adding 20 ml of cord buffer to veins at room temperature, the vein cells separated from the opposite end were collected. The cord buffer was added to the veins again to react at 37° C. The collected HUVECs were washed and poured to the coated T75 flask used for tissue culture with 0.1% of gelatin. The cells were cultured in EGM™-2 complete medium (Cambrex, Md., USA) in 5% $CO_2$ culture incubator at 37° C. and when the cells became to confluent phase, the cells were separated from trypsin-EDTA solution. The cells of 3-4 passages obtained from the above process were used in the experiment.

REFERENCE EXAMPLE 2

Preparation of HUVECs with DKK2 Over-Expression or Silenced DKK2 Expression by Using Lentivirus Vector The DKK2-recombinant viruses, lentivirus containing DKK2 gene or lentivirus containing DKK2 shRNA, were purchased from Macrogen Inc (South Korea). 48 hours after the addition of DKK2 virus to HUVECs prepared in Reference Example 1, the isolated RNA from the cells was performed to reverse-transcription and polymerization to confirm the expression level of DKK2 mRNA as follows: total RNA was isolated using by TRIzol reagent (Invitrogen, USA), performed to reverse transcription using by oligo (dT) primer and following PCR cycles were repeated 30 times using by reverse transcriptase (Stratagen, USA); pre-denaturation at 94° C. for 5 min using by polymerase (Stratagen, USA), denaturation at 94° C. for 30 sec, annealing at 50° C. for 30 sec using by primers and extension at 72° C. for 30 sec.

Figure 43:
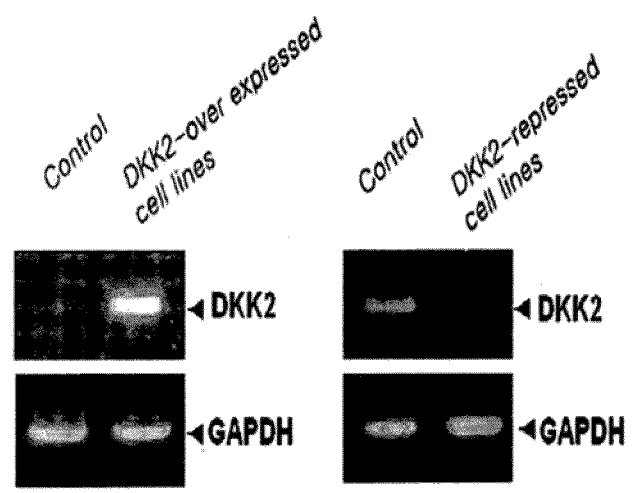
FIG. 43 represents the production result of DKK2 expression cell line and DKK2 repression cell line using by lentiviruses.

As shown in FIG. 43, the results demonstrate that the over-expression cell lines and repression cell lines of DKK2 were well-produced.

REFERENCE EXAMPLE 3

Preparation of DKK2-Transgenic Mouse

Figure 46:
FIG. 46 represents the confirmation of DKK2-transgenic mouse by DNA amplification.

The DKK2 over-expression mouse was prepared using the Tie2 transcription regulatory region activated in only vascular endothelial cells to determine the effect of DKK2 gene on angiogenesis in vivo (Schlaeger T M et al., Proc. Natl. Acad. Sci. USA, 94(7), pp. 3058-3063, 1997). As shown in FIG. 18A, mouse DKK2 gene represented by SEQ ID NO: 28 was treated with Hind III and Not I (NEB, England) and cloned into pSP vector (Clontech, USA). The cloned plasmid was treated with Sal I (NEB, England) to prepare DNA fragments and the prepared DNA fragments were injected into the ovules isolated from the mouse (C57BL6, Orient Inc, Korea) of which ovulation had been stimulated by gonadotropin releasing-hormone (Sigma, USA) to induce transduction, and then, the DKK2-transgenic ovules were implanted on surrogate mother mouse after fertilization. The tail of the mouse born after the 21st fertilization was cut, treated with proteinase K (Sigma, USA) to isolate DNA, and the isolated DNA was amplified by PCR [(pre-denaturation at 94° C. for 5 min, denaturation at 94° C. for 30 sec, annealing at 55° C. for 30 sec and extension at 72° C. for 30 sec)×30 cycles and post-extension at 72° C. for 10 min] using the DKK2 primers represented by SEQ ID NO: 29 and SEQ ID NO: 30 (See FIG. 46).

EXPERIMENTAL EXAMPLE 1

DKK2 Expression Spectra During the Differentiation of Human Umbilical Vein Endothelial Cells 250 µl of Matrigel (Collaborative Biomedical Products, USA; density: 10 mg proteins/ml) was added to the well plates with the diameter of 16 mm and performed to polymerization at 37° C. for 30 min. The HUVECs prepared in Reference Example 1 were cultured in M199 growth medium (Invitrogen, USA) containing 20% (v/v) fetal bovine serum (FBS, Hyclone, USA), 100 units/ml of penicillin (Invitrogen, USA), 10 µg/ml of streptomycin (Invitrogen, USA), 3 ng/ml of bFGF (basic fibroblast growth factor; Upstate Biotechnology, USA) and 5 units/ml of heparin (Sigma, USA) and trypsin was added thereto to obtain cultured cells. The cells were suspended in the growth medium and spread onto Matrigel layer in the concentration of $2 \times 10^5$ cells/well to induce the differentiation of cells (See FIG. 41).

Figure 41:
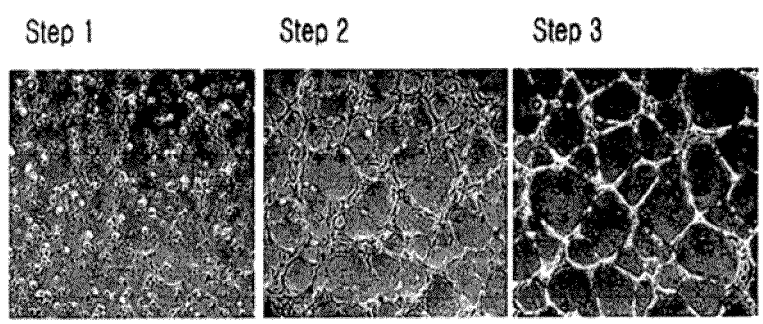
FIG. 41 shows the differentiation feature of the HUVEC (Human umbilical vein endothelial cell) on Matrigel.

As shown in FIG. 41, differentiation consists of 3 steps; the first step is the beginning of differentiation used as control group, the second step is the formation of blood vessel-like structure due to cell transfer and the third step is the completion of blood vessel-like structure formation.

Figure 42:
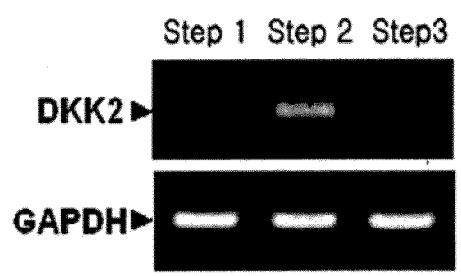
FIG. 42 represents the expression of DKK2 gene on differentiation of the HUVEC.

After isolating RNA from the cells in each step using by TRIZOL solution (Invitrogen, USA), the isolated RNA was performed to reverse transcription using the primers represented by SEQ ID NO: 31 and SEQ ID NO:32, and amplification according to the process disclosed in Reference Example 3 (See FIG. 42).

As shown in FIG. 42, the results demonstrate that the expression of DKK2 genes was increased during the tube formation. It has been confirmed that the DKK2 is positive regulator of tube formation.

EXPERIMENTAL EXAMPLE 2

The Effect of DKK2 on Tube Formation of Human HUVECs

250 µl of Matrigel (Collaborative Biomedical Products, USA; density: 10 mg proteins/ml) was added to the well plates with the diameter of 16 mm and performed to polymerization at 37° C. for 30 min. The HUVECs prepared in Reference Example 2 were cultured in M199 growth medium (Invitrogen, USA) containing 20% (v/v) fetal bovine serum (FBS, Hyclone, USA), 100 units/ml of penicillin (Invitrogen, USA), 10 µg/ml of streptomycin (Invitrogen, USA), 3 ng/ml of bFGF (basic fibroblast growth factor; Upstate Biotechnology, USA) and 5 units/ml of heparin (Sigma, USA) and trypsin was added thereto to obtain cultured cells. The cells were suspended in the growth medium and spread onto Matrigel layer in the concentration of $2 \times 10^5$ cells/well to induce the differentiation of cells (See FIG. 44). Then, the cells were cultured for 20 hours. The rate of tube formation was measured by an optical microscopy (ZEISS, Germany) and the group which was not treated with DKK2 was regarded as a negative control group.

Figure 44:
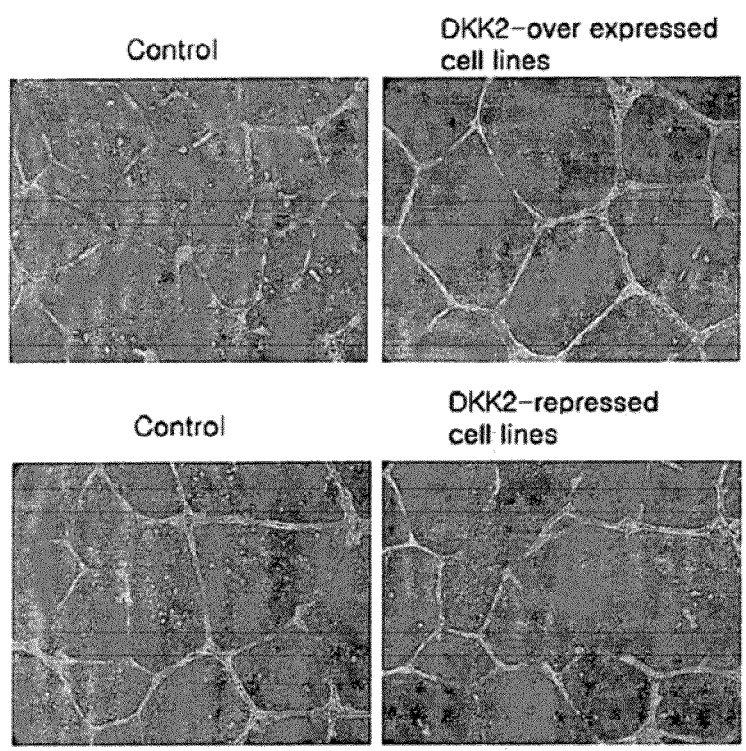
FIG. 44 shows the comparison result of tube formation on DKK2 expression and repression cell lines.

As shown in FIG. 44, the results demonstrate that the tube formation was induced on expression cell line of DKK2, but decreased on repression cell line of DKK2.

EXPERIMENTAL EXAMPLE 3

The Stabilization Effect of DKK2 on β-Catenin

The over-expression cell lines of DKK2 using by lentivirus system prepared in Reference Example 2 were cultured for 24 hrs. The medium was replaced into M199 growth medium containing 20% (v/v) of fetal bovine serum (FBS, Hyclone, USA), 100 units/ml of penicillin (Invitrogen, USA), 10 µg/ml of streptomycin (Invitrogen, USA), 3 ng/ml of bFGF (basic fibroblast growth factor; Upstate Biotechnology, USA) and 5 units/ml of heparin (Sigma, USA), and 200 ng/ml sFrizzled (BD bioscience, USA) was added thereto as a Wnt secretion inhibitor. After culturing for 24 hrs, trypsin was treated thereto to obtain the cultured cells. DNA was separated from the cells using by lysis buffer containing 100 mM of Tris/Cl, 5 mM of EDTA, 50 mM of beta-glycerophosphate, 50 mM of NaF, 100 µM of Na$_3$VO4, 1 mM of PMSF, 0.5% of NP-40 and 1% of Triton X-100. The expression level of the separated DNA was confirmed through the western blot test using by the antibody of β-catenin (Upstate Biotechnology, USA).

Figure 45:
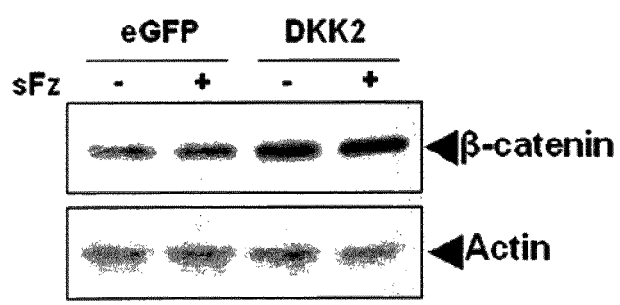
FIG. 45 represents the increasing result of β-catenin protein by the treatment of DKK2 distinct from Wnt signal.

As shown in FIG. 45, the expression level of β-catenin protein was significantly increased by DKK2 compared with control group (eGFP), and the increased level was not reduced in spite of the treatment of Wnt repressor (sFz). Accordingly, it has been confirmed that DKK2 stimulates the angiogenesis by controlling the expression level of β-catenin protein as distinct from Wnt signal.

EXPERIMENTAL EXAMPLE 4

The Effect of DKK2 on the Sprouting of Endothelial Cells from Aorta of DKK2-Transgenic Mouse The aorta which had been isolated from the back region of DKK2-transgenic mouse prepared in Reference Example 3 and 6-weeks-old normal mouse were cut into the size of 1 mm and the arterial circle tissues were laid on 48-well plates coated with 110 µl of matrigel. The well was sealed again with 40 µl of Matrigel and HUVEC culture medium (SFM, Invitrogen, USA) was added to each well to the extent the final volume of each well reached to 200 µl. After 5 days, the number of sprout formed from each circle was counted and the rate of sprout in DKK2-transgenic mouse group was compared with that in control mouse group (See FIG. 47). The rate of sprout was scored by dividing the sprout into five parts according to following criteria; 5 points was assigned in case that all the 5 parts were sprouted, 0 points was assigned in case that none was sprouted.

Figure 47:
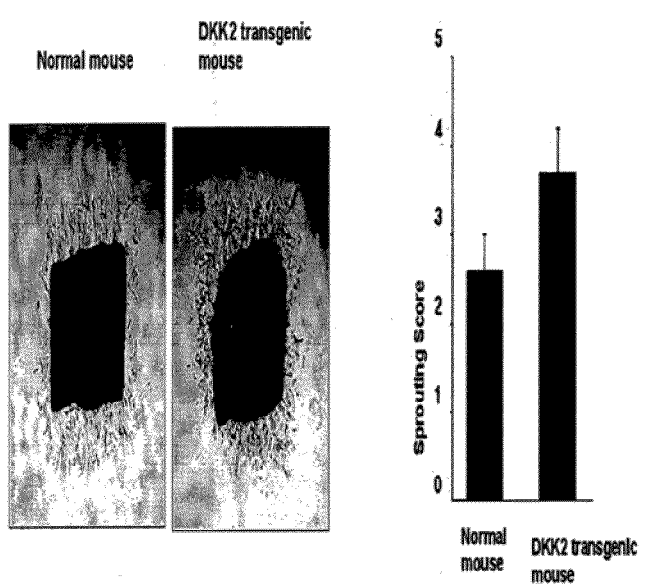
FIG. 47 presents the induction of the sprouting of endothelial cells from aorta of DKK2-transgenic mouse

As can be seen in FIG. 47, the result demonstrates that the sprouting of the arterial circle tissues in DKK2-transgenic mouse was significantly increased compared with that in normal mouse.

EXPERIMENTAL EXAMPLE 5

The Effect of DKK2 on the Development of Blood Vessel in the Embryo of DKK2-Transgenic Mouse The embryos delivered from the 9th to 10th pregnant normal and DKK2-transgenic mice were fixed with 4% paraformaldehyde for a day and stained with the antibody of von Willebrand Factor (Vwf) (Chemicon, USA) specifically expressed only on vascular endothelial cells to observe the development of blood vessel by the method disclosed in literature (Sadler J. E., J. Thromb. Haemost., 3(8), pp 1702-1709, 2005).

Figure 48:
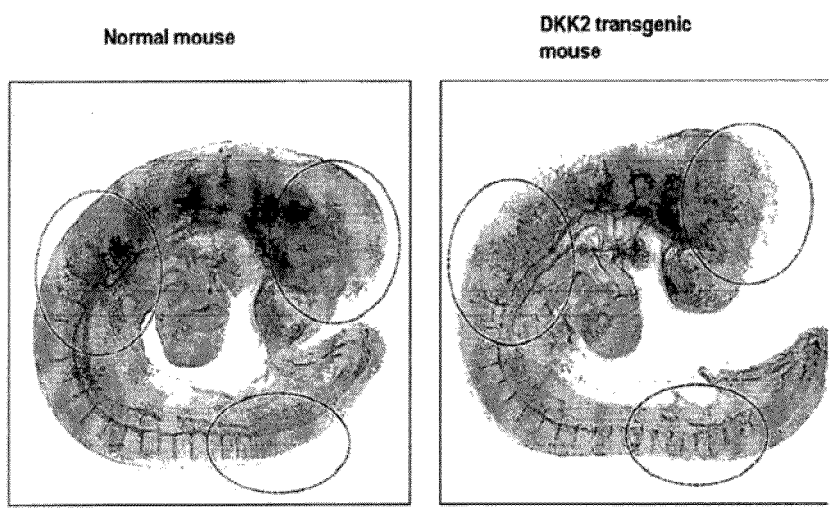
FIG. 48 shows the vessel development on embryo of normal mouse and DKK2-transgenic mouse using the antibody of vWF which is vessel-specific protein.

As can be seen in FIG. 48, the results demonstrate that angiogenesis and vascular development are generally increased in the embryo of DKK2-transgenic mouse compared with the normal mouse control.

To verify the effect of DKK2 on the angiogenesis of embryo, the development of head capillary plexus, descending aorta and segmental vessels in the embryos prepared by the above-described process was determined by high magnification.

Figure 49:
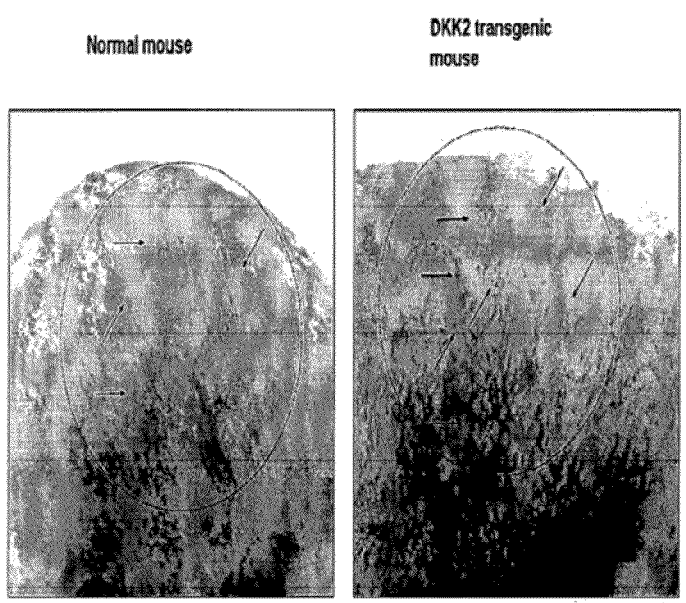
FIG. 49 shows the comparison results of angiogenesis on the head region of embryo of normal mouse and DKK2-transgenic mouse.
Figure 50:
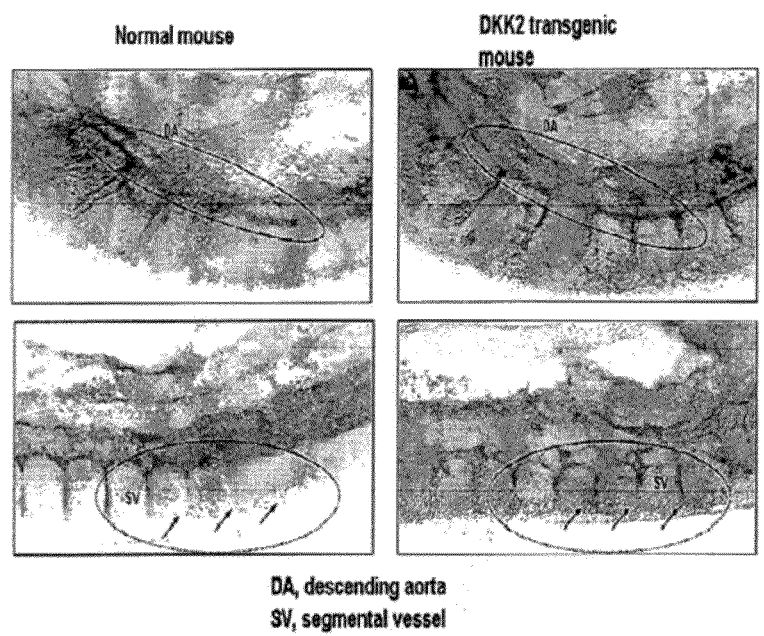
FIG. 50 presents the growth of descending aorta and segmental vessel on the embryo of normal mouse and DKK2-transgenic mouse.

As shown in FIGS. 49 and 50, the results demonstrate that the significantly enhanced growth of head capillary plexus and segmental vessel and enlarged descending aorta on embryos of DKK2-transgenic mouse was promoted.

According to a composition and method of promoting angiogenesis of the present invention, angiogenesis in vitro or in vivo may be efficiently promoted.

According to a composition and method of promoting filopodia motility in an endothelial cell of the present invention, filopodia motility in an endothelial cell may be efficiently promoted.

According to a composition and method of promoting angiogenic sprouting of the present invention, angiogenic sprouting may be efficiently promoted.

According to a composition and method of preventing or treating ischemic diseases, ischemic diseases may be efficiently prevented or treated.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of promoting angiogenesis in a subject, the method comprising:
    administering to subject a composition comprising at least one of DKK2 and DKK2-Fc fusion protein, wherein the subject has a vascular unformed tissue.

2. The method of claim 1, wherein the subject has an ischemic vascular disease.

3. The method of claim 2, wherein the ischemic vascular disease is selected from the group consisting of a burn, psoriasis, an ulcer, myocardial infarction, angina pectoris, cerebral infarction, and cerebral hemorrhage.

4. A method of promoting filopodia motility in an endothelial cell in a subject, the method comprising:
    administering to the subject a composition comprising at least one of DKK2 and DKK2-Fc fusion protein, wherein the subject has a vascular unformed tissue.

5. A method of promoting angiogenic sprouting in a subject, the method comprising:
    administering to the subject a composition comprising at least one of DKK2 and DKK2-Fc fusion protein, wherein the subject has a vascular unformed tissue.

6. A method of treating an ischemic disease in a subject, the method comprising:
    administering to the subject a composition comprising at least one of DKK2 and DKK2-Fc fusion protein, wherein the subject has a vascular unformed tissue.

7. The method of claim 6, wherein the ischemic disease is selected from the group consisting of a burn, psoriasis, an ulcer, angina pectoris, cerebral infarction, cerebral hemorrhage and myocardial infarction.

* * * * *